United States Patent
Kunuki et al.

(10) Patent No.: US 7,450,236 B2
(45) Date of Patent: *Nov. 11, 2008

(54) MEASURING APPARATUS AND SENSOR UNIT FOR SAME

(75) Inventors: Yoshiyuki Kunuki, Kanagawa-ken (JP);
Hitoshi Shimizu, Kanagawa-ken (JP);
Toshihito Kimura, Kanagawa-ken (JP)

(73) Assignee: FUJIFILM Corporation, Tokyo (JP)

( * ) Notice: Subject to any disclaimer, the term of this patent is extended or adjusted under 35 U.S.C. 154(b) by 343 days.

This patent is subject to a terminal disclaimer.

(21) Appl. No.: 10/932,071

(22) Filed: Sep. 2, 2004

(65) Prior Publication Data

US 2005/0046854 A1 Mar. 3, 2005

(30) Foreign Application Priority Data

| Sep. 2, 2003 | (JP) | ............................. 2003-309968 |
| Sep. 2, 2003 | (JP) | ............................. 2003-309969 |
| Sep. 2, 2003 | (JP) | ............................. 2003-310058 |

(51) Int. Cl.
*G01N 21/55* (2006.01)
(52) U.S. Cl. ..................................... 356/445
(58) Field of Classification Search .................. 356/445
See application file for complete search history.

(56) References Cited

U.S. PATENT DOCUMENTS 7,144,153 B2 * 12/2006 Sato ........................... 356/445

| 2001/0040680 A1 | 11/2001 | Kubo et al. |
| 2002/0140938 A1 * | 10/2002 | Naya et al. ................. 356/445 |
| 2003/0113231 A1 * | 6/2003 | Karube et al. ............ 422/82.05 |
| 2006/0017931 A1 * | 1/2006 | Kimura ..................... 356/445 |

FOREIGN PATENT DOCUMENTS

| EP | 0 953 836 A2 | 11/1999 |
| EP | 1 154 259 A1 | 11/2001 |
| EP | 1 243 916 A2 | 9/2002 |

(Continued)

OTHER PUBLICATIONS

"Surface Refracto-Sensor using Evanescent Waves: Principles and Instrumentations" by Takayuki Okamoto (Spectrum Researches, vol. 47, No. 1 (1998), pp. 21 to 23 & pp. 26 and 27), Abstract.

(Continued)

*Primary Examiner*—Gregory J Toatley, Jr.
*Assistant Examiner*—Juan D Valentin
(74) *Attorney, Agent, or Firm*—Sughrue Mion, PLLC

(57) ABSTRACT

A sensor unit includes a dielectric block, a thin film layer and a reference surface. The thin film layer is formed on the upper surface of the dielectric block and the reference surface is coplanar with the upper surface of the dielectric block. The sensor unit is held in a predetermined position. A light beam is caused to enter the dielectric block to impinge upon the interface between the upper surface of the dielectric block and the thin film layer so that total internal reflection conditions are satisfied at the interface. Information on an analyte on the thin film layer is obtained on the basis of the light beam reflected at the interface. Displacement of the interface is measured by measuring displacement of the reference surface and the position of the sensor unit is adjusted according to the displacement of the reference surface.

37 Claims, 19 Drawing Sheets

FOREIGN PATENT DOCUMENTS

JP 6-167443 A 6/1994

OTHER PUBLICATIONS

"Porous Gold in Surface Plasmon Resonance Measurement" by D.V. Noort, K. Johansen, and C.F. Mandenius (Eurosensors XIII, 1999, pp. 585-588).

"Surface Plasmon Resonance Interferometry for Micro-Array Biosensing" by P.I. Nikitin, A.N. Grigorenko, A.A. Beloglazov, M.V. Valeiko, A.I. Savchuk, and O.A. Savchuk (Eurosensors XIII, 1999, pp. 235-238).

\* cited by examiner

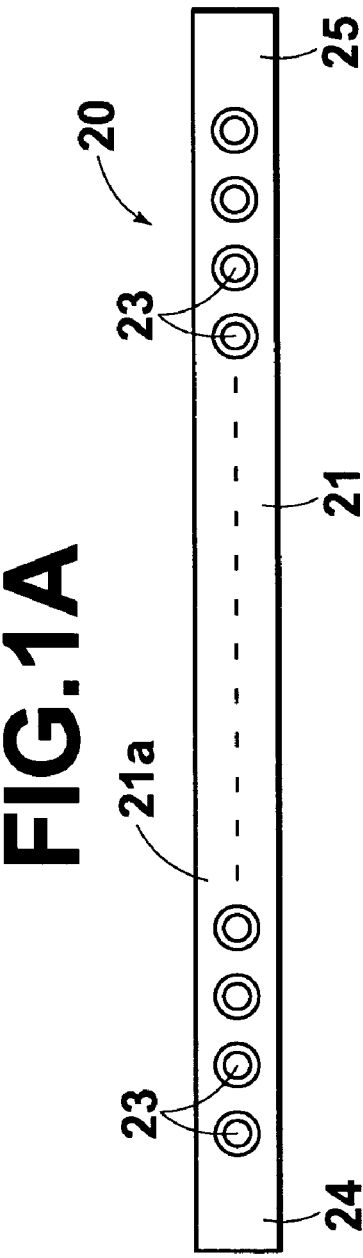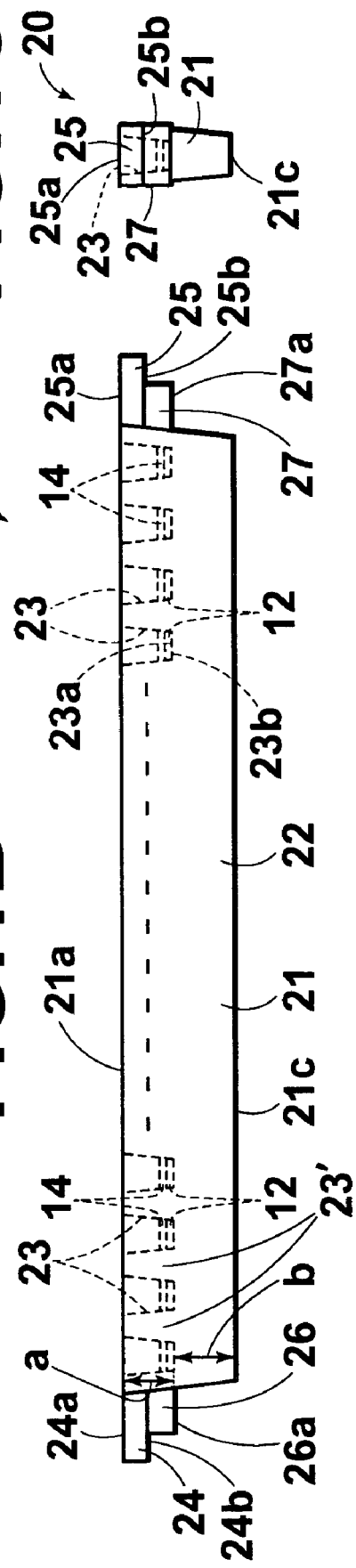

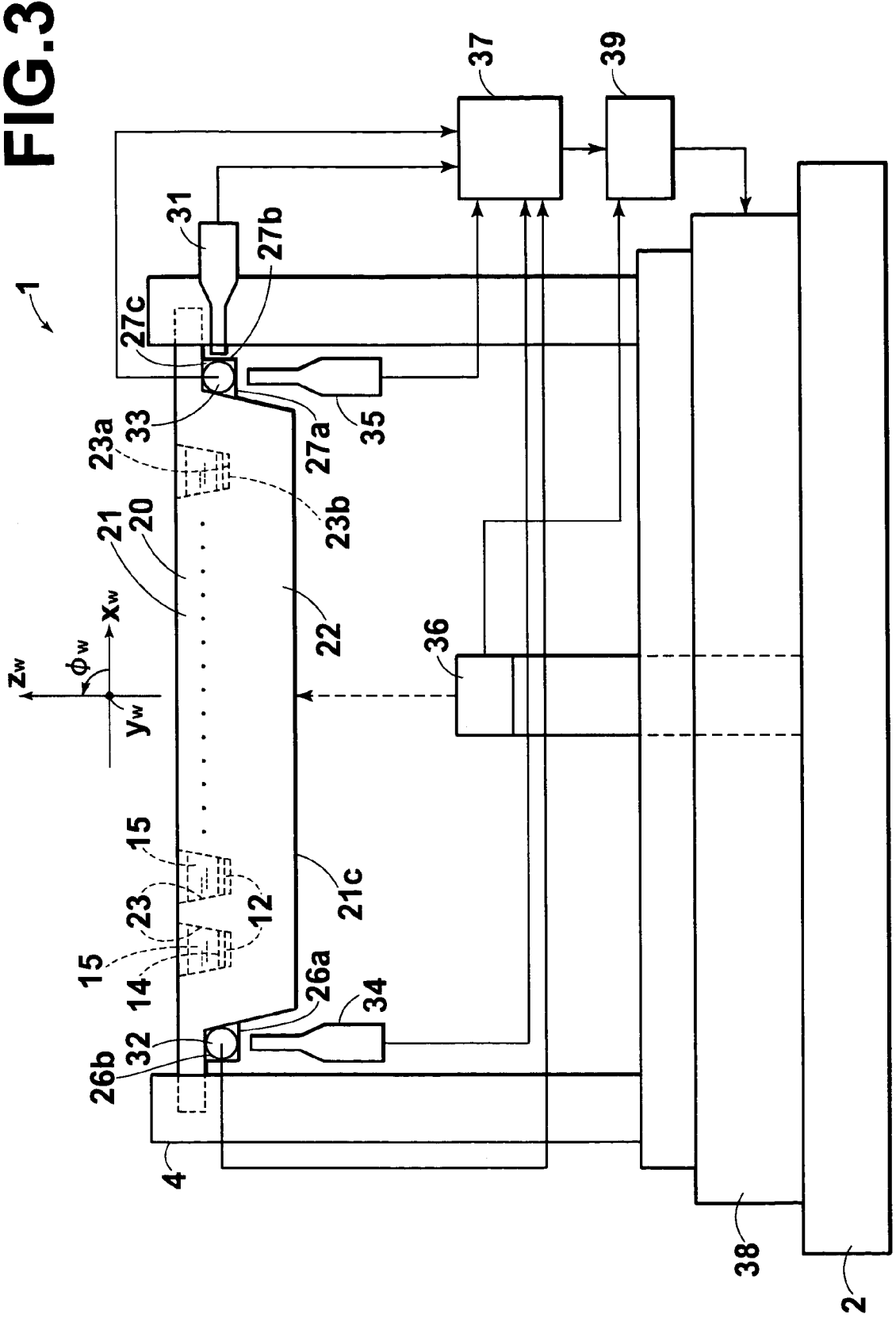

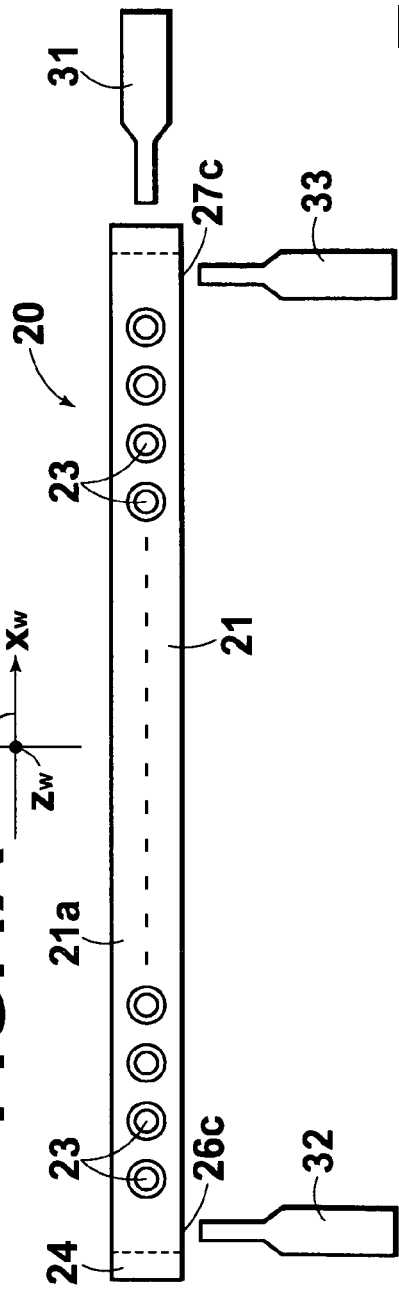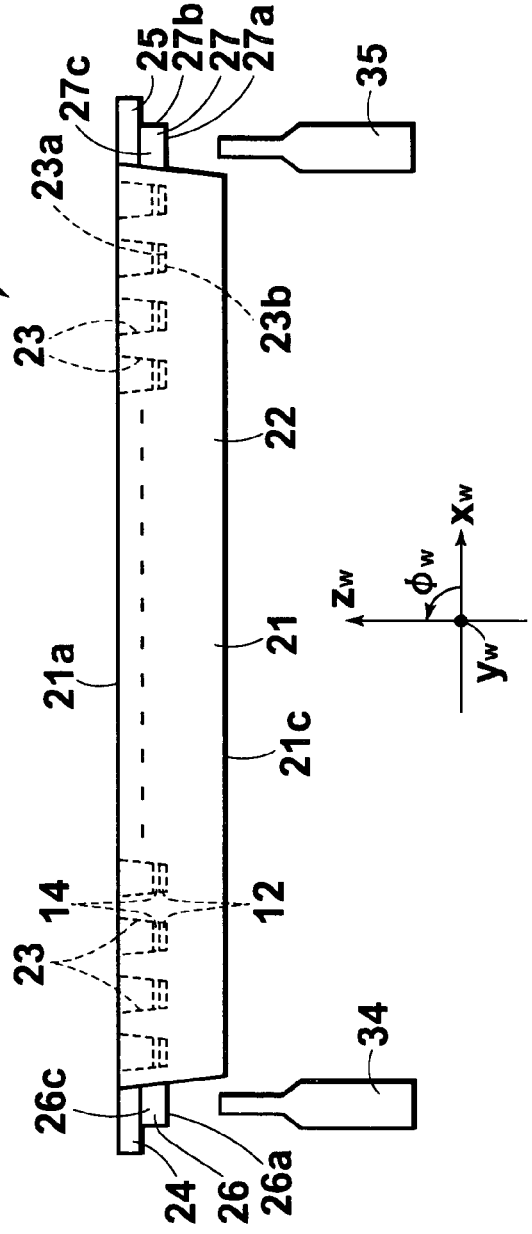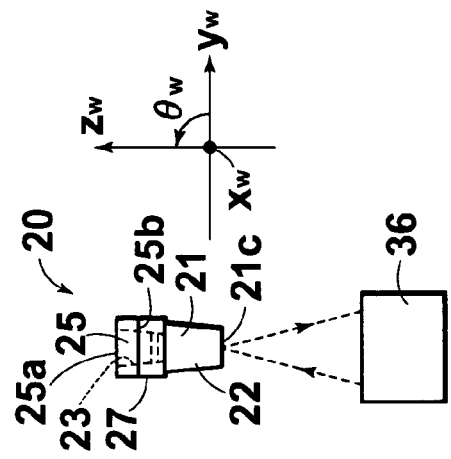

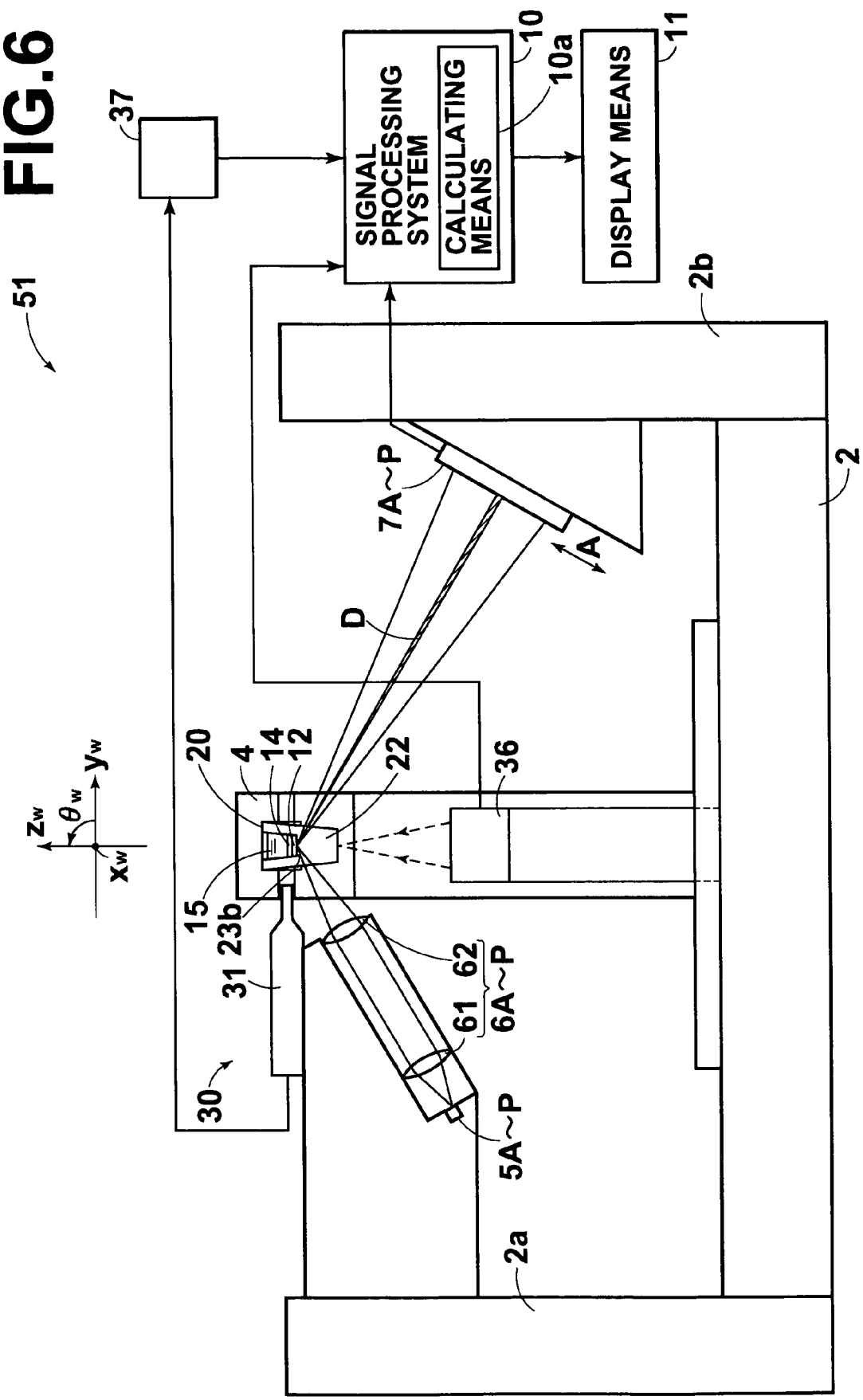

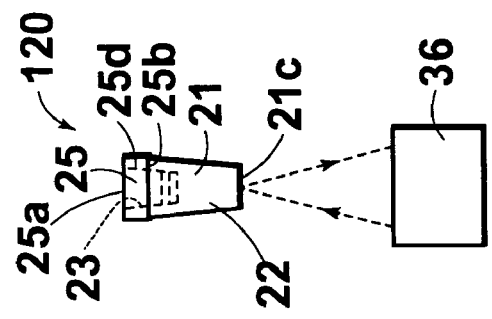
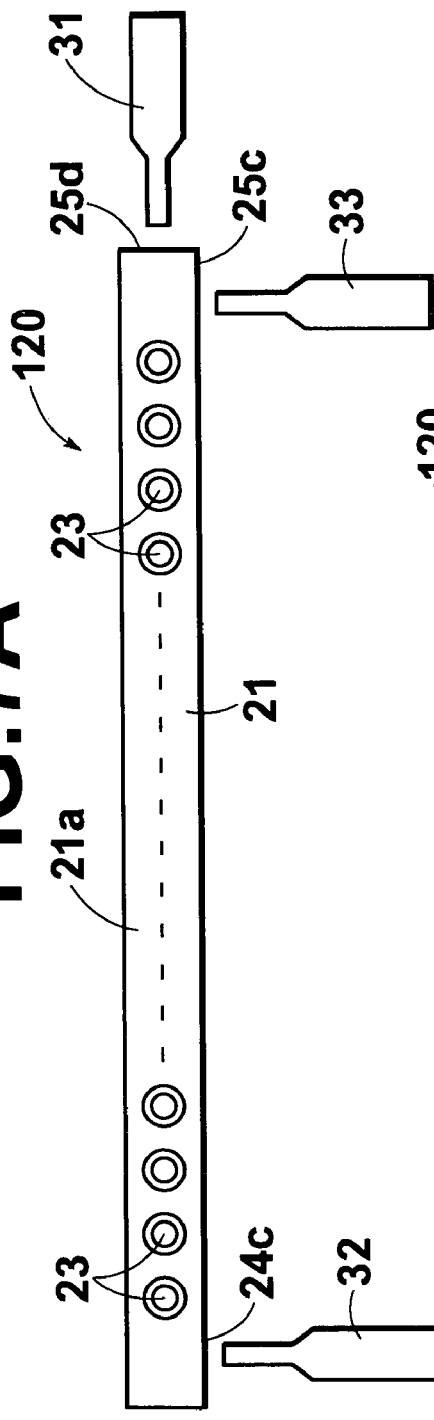
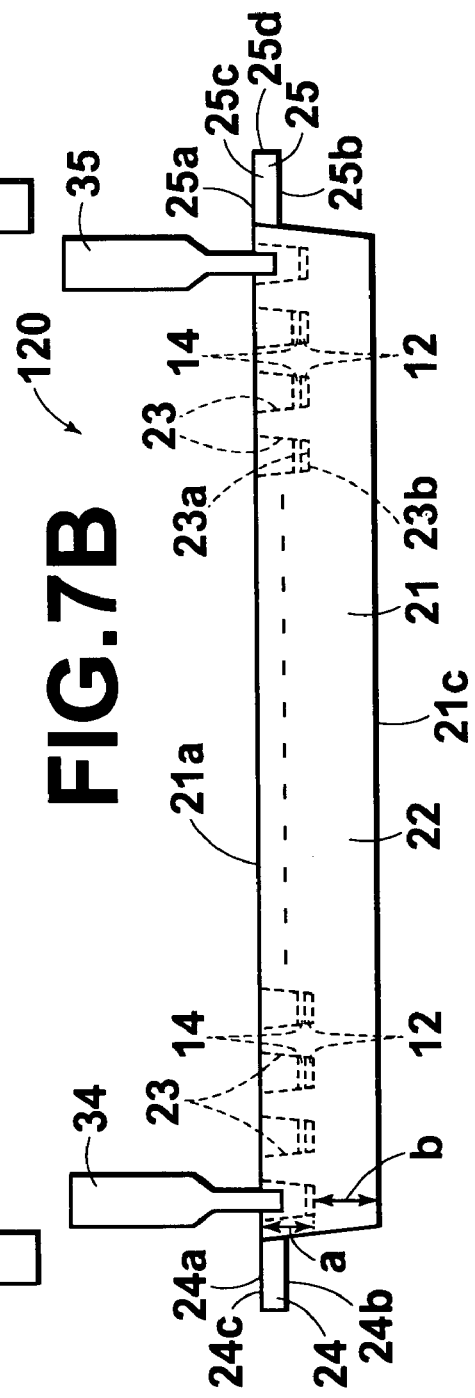

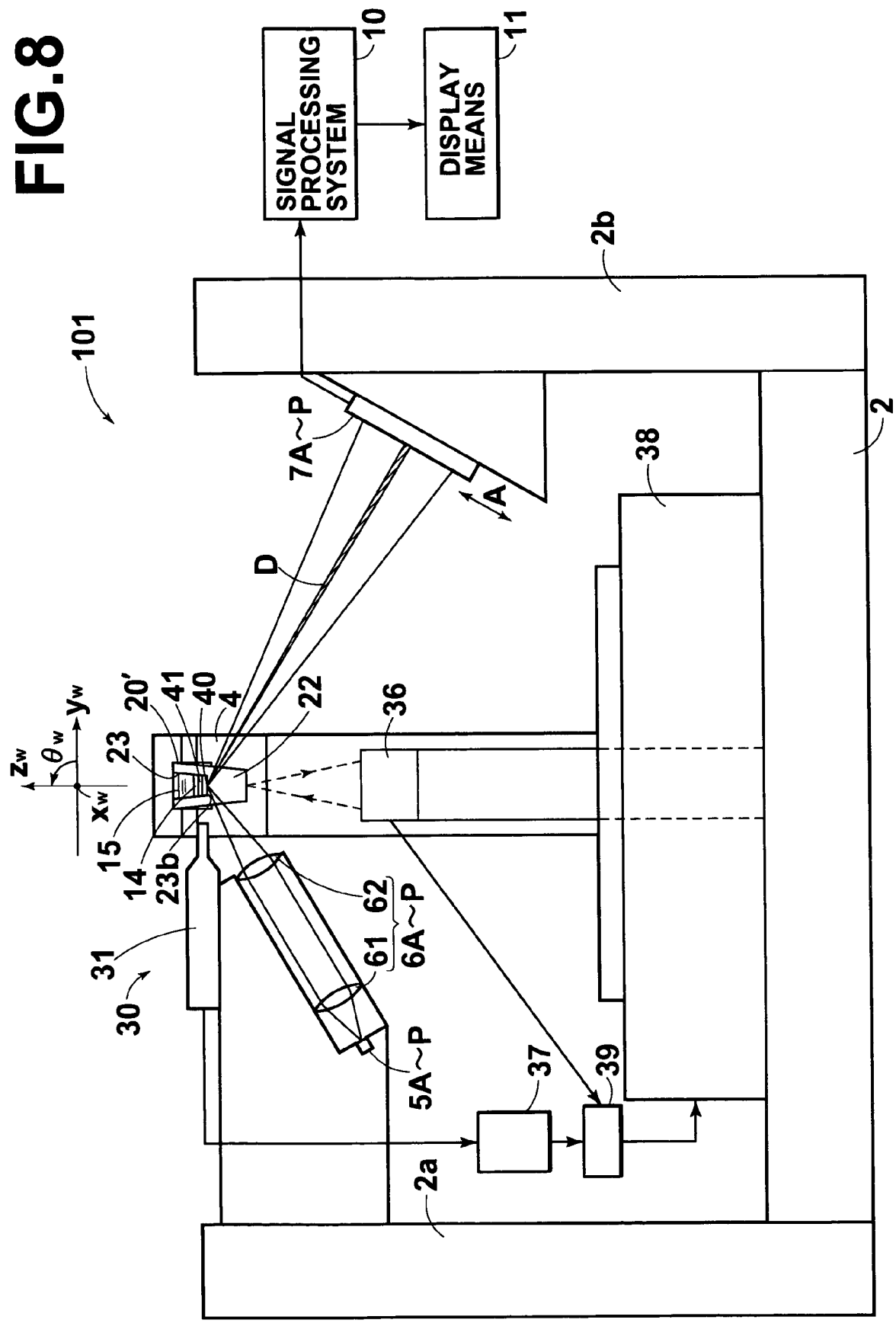

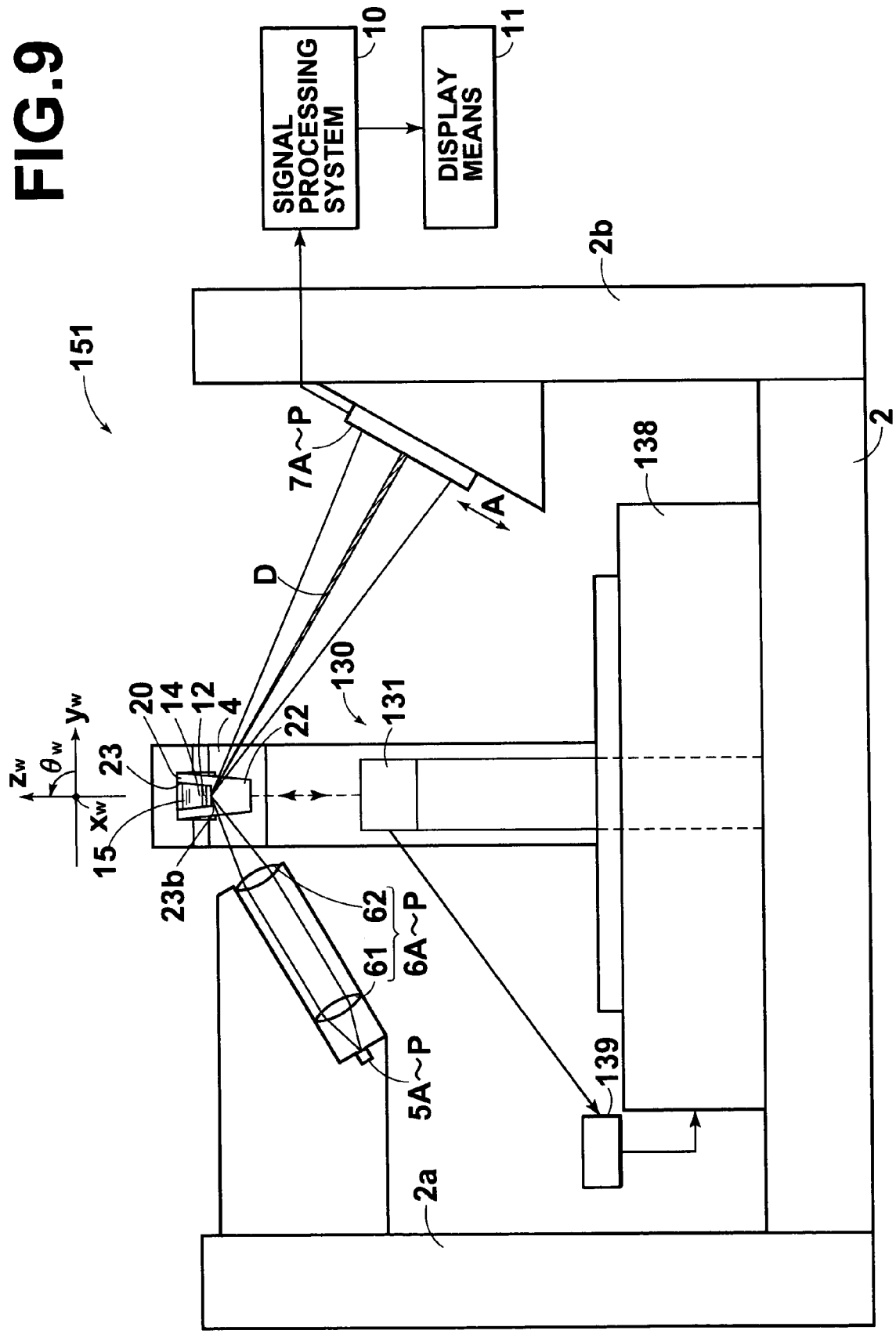

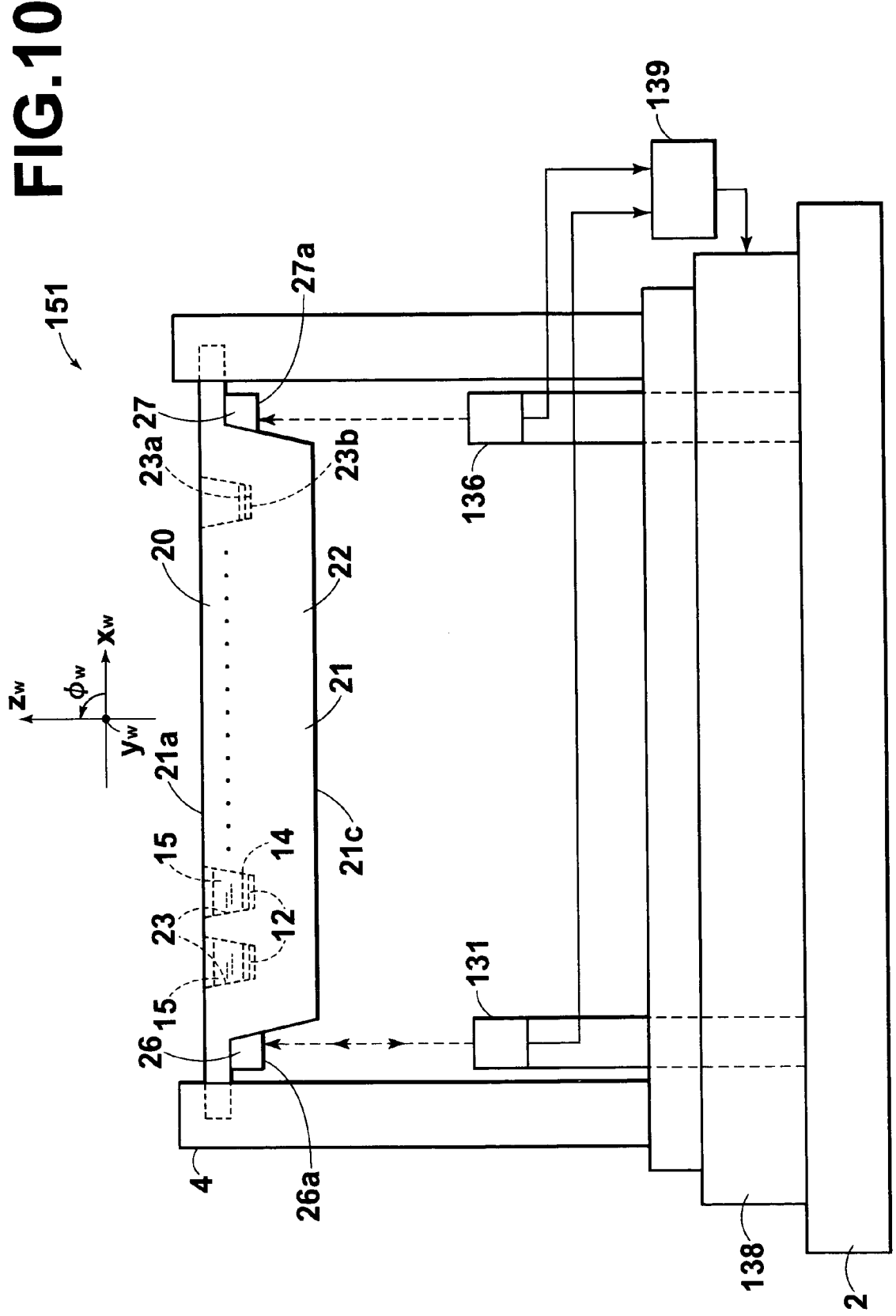

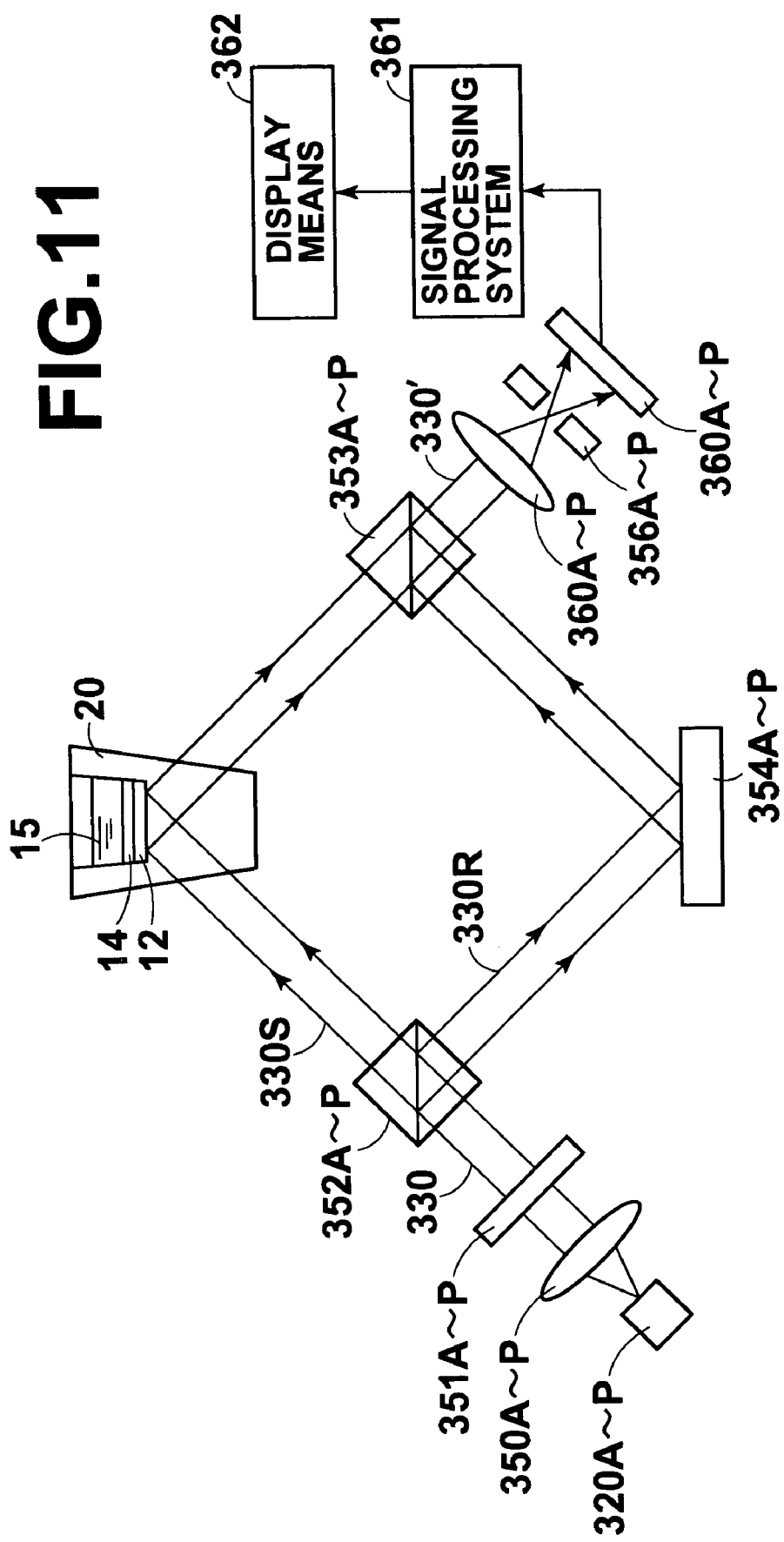

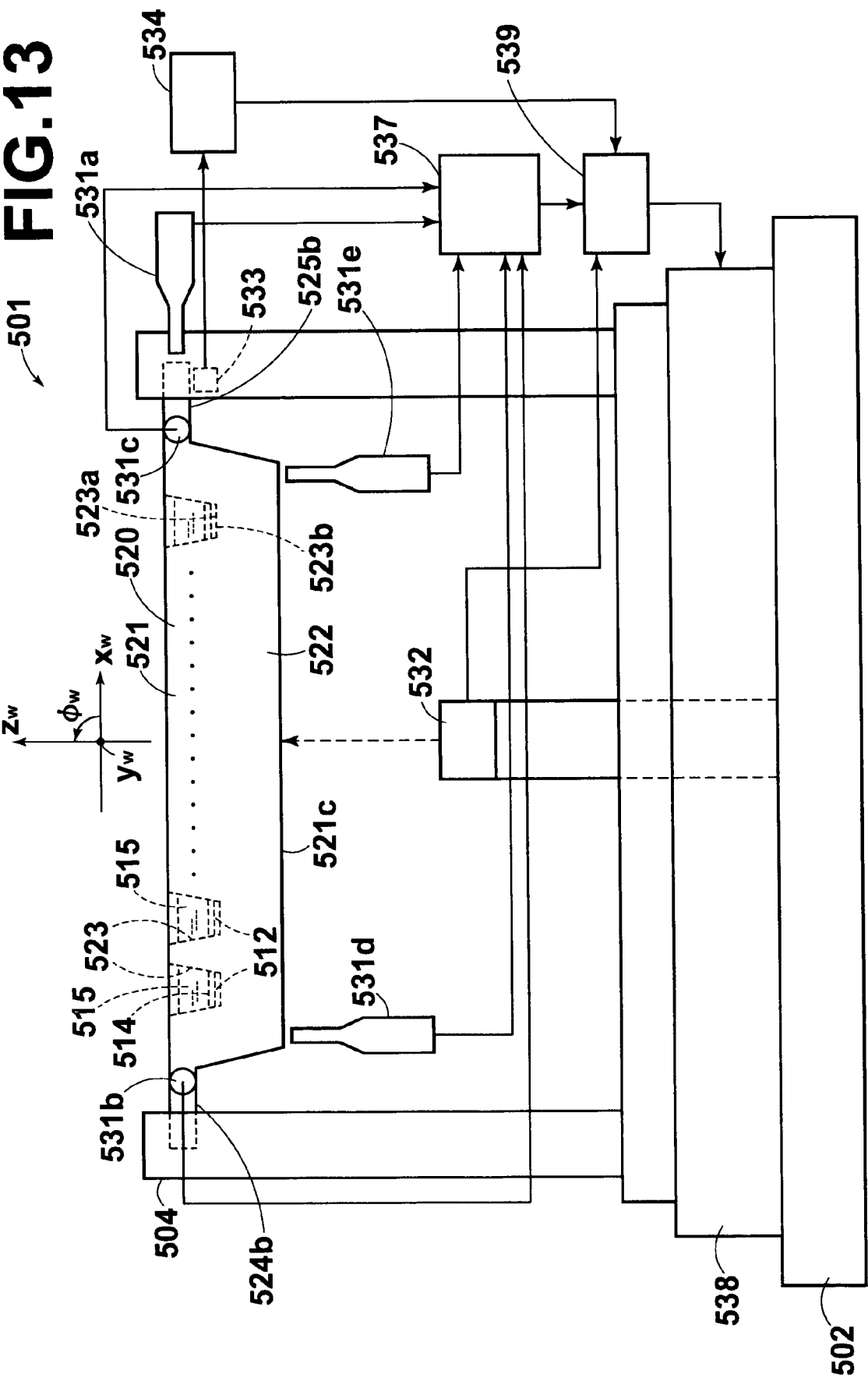

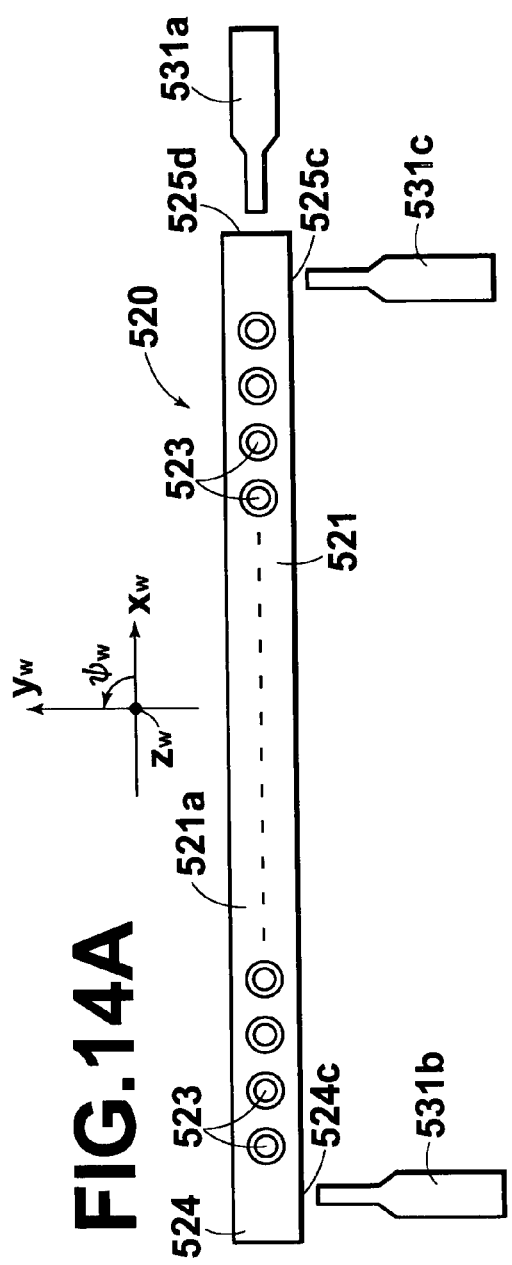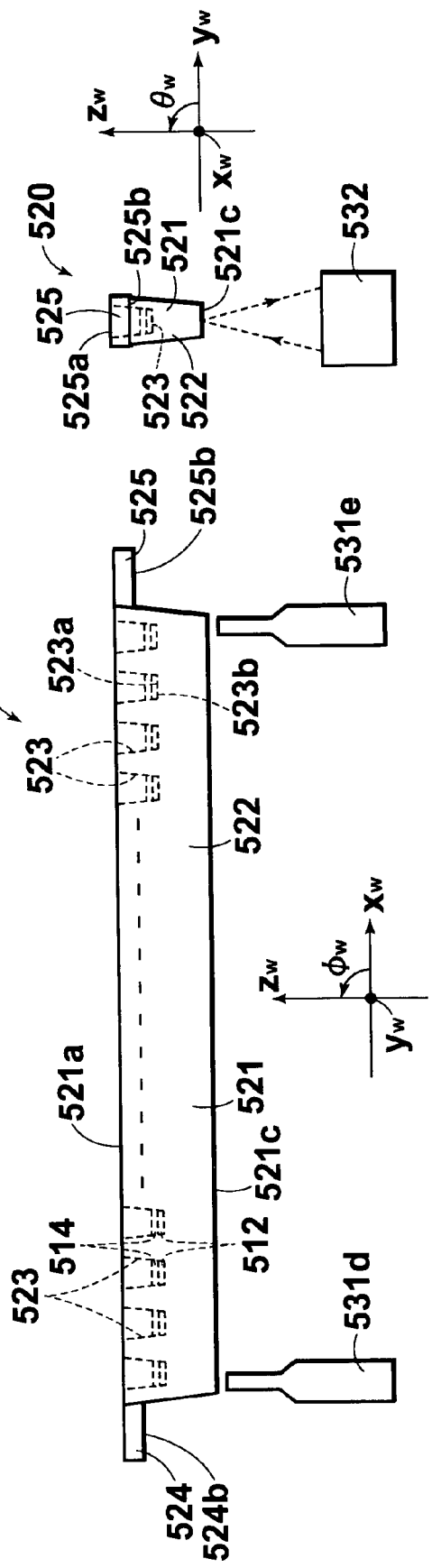

MEASURING APPARATUS AND SENSOR UNIT FOR SAME

BACKGROUND OF THE INVENTION

1. Field of the Invention

This invention relates to a measuring apparatus such as a surface plasmon resonance sensor for analyzing a material in a sample on the basis of generation of surface plasmon, and to a sensor unit for the measuring apparatus.

2. Description of the Related Art

In metal, free electrons vibrate in a group to generate compression waves called plasma waves. The compression waves generated in a metal surface are quantized into surface plasmon.

There have been proposed various surface plasmon resonance sensors for quantitatively analyzing a material in a sample utilizing a phenomenon that such surface plasmon is excited by light waves. Among those, one employing a system called "Kretschmann configuration" is best known. See, for instance, Japanese Unexamined Patent Publication No. 6(1994)-167443.

The surface plasmon resonance sensor using the Kretschmann configuration basically comprises a dielectric block shaped, for instance, like a prism, a metal film which is formed on one face of the dielectric block and is brought into contact with a sample, a light source emitting a light beam, an optical system which causes the light beam to enter the dielectric block at various angles of incidence so that total internal reflection conditions are satisfied at the interface of the dielectric block and the metal film and various angles of incidence of the light beam to the interface of the dielectric block and the metal film including an angle of incidence at which attenuation in total internal reflection is generated due to surface plasmon resonance (the attenuation angle) can be obtained, and an information obtaining means which detects the intensity of the light beam reflected in total internal reflection at the interface and obtains information on the attenuation angle and the change thereof.

In order to obtain various angles of incidence of the light beam to the interface, a relatively thin incident light beam may be caused to impinge upon the interface changing the angle of incidence or a relatively thick incident light beam may be caused to impinge upon the interface in the form of convergent light or divergent light so that the incident light beam includes components impinging upon the interface at various angles. In the former case, the light beam which is reflected from the interface at an angle which varies as the angle of incidence changes may be detected by a photodetector which is moved in synchronization with the change of the angle of incidence or by an area sensor extending in the direction in which reflected light beam is moved as the angle of incidence changes. In the latter case, an area sensor which extends in directions so that all the components of light reflected from the interface at various angles can be detected by the area sensor may be used.

In such a surface plasmon resonance sensor, when a light beam impinges upon the metal film at a particular angle of incidence θsp not smaller than the angle of total internal reflection, evanescent waves having an electric field distribution in the sample in contact with the metal film are generated and surface plasmon is excited in the interface between the metal film and the sample. When the wave vector of the evanescent light is equal to the wave number of the surface plasmon and wave number matching is established, the evanescent waves and the surface plasmon resonate and light energy is transferred to the surface plasmon, whereby the intensity of light reflected in total internal reflection at the interface of the dielectric block and the metal film sharply drops. The sharp intensity drop is generally detected as a dark line by the photodetector.

The aforesaid resonance occurs only when the incident light beam is p-polarized. Accordingly, it is necessary to set the surface plasmon sensor so that the light beam impinges upon the interface in the form of p-polarized light or p-polarized components are only detected.

When the wave number of the surface plasmon can be known from the angle of incidence θsp at which the phenomenon of attenuation in total internal reflection (ATR) takes place, the dielectric constant of the sample can be obtained. That is, $$K_{sp}(\omega) = \frac{\omega}{c} \sqrt{\frac{\varepsilon_m(\omega)\varepsilon_s}{\varepsilon_m(\omega) + \varepsilon_s}}$$

wherein $K_{sp}$ represents the wave number of the surface plasmon, ω represents the angular frequency of the surface plasmon, c represents the speed of light in a vacuum, and ∈m and ∈s respectively represent the dielectric constants of the metal and the sample.

When the dielectric constant ∈s of the sample is known, the concentration of a specific material in the sample can be determined on the basis of a predetermined calibration curve or the like. Accordingly, the specific material in the sample can be quantitatively analyzed by detecting the angle of incidence θsp at which the intensity of light reflected in total internal reflection from the interface of the prism and the metal film sharply drops (this angle θsp is generally referred to as "the attenuation angle θsp").

As a similar apparatus utilizing the phenomenon of attenuation in total internal reflection (ATR), there has been known a leaky mode sensor described in, for instance, "Surface Refracto-Sensor using Evanescent Waves: Principles and Instrumentations" by Takayuki Okamoto (Spectrum Researches, Vol. 47, No. 1 (1998), pp21 to 23 & pp26 and 27). The leaky mode sensor basically comprises a dielectric block shaped, for instance, like a prism, a clad layer which is formed on one face of the dielectric block, an optical waveguide layer which is formed on the clad layer and is brought into contact with a sample, a light source emitting a light beam, an optical system which causes the light beam to enter the dielectric block at various angles of incidence so that total internal reflection conditions are satisfied at the interface of the dielectric block and the clad layer and attenuation in total internal reflection is generated due to optical waveguide mode excitation can be obtained, and an information obtaining means which detects the intensity of the light beam reflected in total internal reflection at the interface and obtains information on the state of waveguide mode excitation (the attenuation angle and the change thereof.

In the leaky mode sensor with this arrangement, when the light beam is caused to impinge upon the clad layer through the dielectric block at an angle not smaller than an angle of total internal reflection, evanescent waves are generated in the optical waveguide layer and an evanescent wave having a particular wave number comes to propagate through the optical waveguide layer in a waveguide mode. When the waveguide mode is thus excited, almost all the incident light which generates the evanescent wave having a particular wave number is taken in the optical waveguide layer and accordingly, the intensity of light reflected in total internal reflection at the interface of the dielectric block and the clad layer sharply drops. That is, attenuation in total internal reflection occurs. Since the wave number of light to be propagated through the optical waveguide layer depends upon the refractive index of the sample on the optical waveguide layer, the refractive index and/or the properties of the sample related to the refractive index can be detected on the basis of the attenuation angle θsp at which the attenuation in total internal reflection occurs.

Such a measuring apparatus is employed, as a biosensor, to analyze a sample, that is, a sensing medium (e.g. antibody), which combines with a particular material (e.g., antigen), is disposed on the thin film (the metal film in the case of a surface plasmon resonance sensor, and optical waveguide layer in the case of a leaky mode sensor) and whether the sample includes a material combined with the sensing medium or the state of combination of the sample with the sensing medium is detected. As a method of analyzing a sample in this way, there has been proposed a method in which, in order to eliminate the influence of the solvent in the sample liquid on the refractive index of the sample liquid, refractive index information on buffer (the same as the solvent) free from the analyte (material to be analyzed) is first obtained and then the sample liquid is dispensed to the buffer to measure the refractive index information of the mixture after the reaction, whereby only the reaction of the analyte is precisely extracted.

As the surface plasmon resonance sensor, there have been known various types of sensors, as well as those in which the attenuation angle is detected, such as those in which light beams of different wavelengths are caused to impinge upon the interface and the degree of attenuation in total internal reflection is detected by the wavelength, or in which a light beam is caused to impinge upon the interface and a part of the light beam is split before the light beam impinges upon the interface and caused to interfere with the other part of the light beam reflected at the interface, thereby measuring the state of interference. Any one of the sensors is a sensor which indirectly obtains information on the refractive index of the analyte on the thin film and the change thereof and analyzes the analyte.

In order to increase efficiency of handling, for instance, in changing the sample in the measuring apparatus, there has been proposed in U.S. Patent Laid-Open No. 20010040680 a sensor well unit comprising a dielectric block, a thin film disposed on the upper surface of the dielectric block and a sample holding portion for holding the sample on the thin film, which are formed integrally with each other. The sensor unit is formed by providing a unit body in the form of a dielectric block with a sample well (sample holding portion) open in the upper surface, and by providing a film layer on the inner bottom surface of the sample well, and the part of the well body below the sample well functions as the known dielectric block which performs the duty of the light beam input-out system. In order to perform measurement on a number of samples at high speed, and to further increase efficiency of handling, there has been proposed a sensor unit formed by providing a unit body in the form of a bar-like or plate-like dielectric block with a plurality of one-dimensionally or two-dimensionally arranged sample wells open in the upper surface. A plurality of light beams are caused to impinge upon the plurality of sample wells in parallel and the reflected light reflected at the interface of each of the sample wells is separately detected.

It is sometimes necessary to perform measurement a plurality of times on a sample at intervals and to detect the change of the state. In such a case, in order to perform such measurement on a plurality of samples at high efficiency, there sometimes employed batch processing in which a first sensor unit is once demounted from the measuring portion (sensor holding portion) of a measuring apparatus after a first measurement on the sample placed in its sample well, another or a second sensor unit is mounted on the measuring portion of the measuring apparatus, and then the first sensor unit is mounted again on the measuring portion of the measuring apparatus after measurement on the samples placed in the sample wells of the second senor unit. Conventionally, there has been a problem that the position of the interface changes each time the same sensor unit is mounted on the measuring portion, which can result in a measuring error.

As a method of dealing with vertical displacement of the interface, there has been proposed a method in which vertical displacement of the outer bottom surface of the sensor unit is measured with the outer bottom surface of the sensor unit taken as a reference plane, and the vertical position of the sensor unit is adjusted on the basis of the vertical displacement of the outer bottom surface of the sensor unit.

However, these inventor's investigation has revealed that even if the vertical position of the sensor unit is adjusted on the basis of the vertical displacement of the outer bottom surface of the sensor unit, there remains a measuring error (an error produced when the state of light reflected in total internal reflection is measured) due to vertical displacement of the interface.

That is, the difference in the vertical direction between the position of the outer bottom surface of the sensor unit and the position of the interface (which is an actual surface of measurement) causes an error in measurement of the vertical position of the interface due to thermal expansion of the sensor unit in response to change in temperature. The distance between the outer bottom surface of the sensor unit and the inner bottom surface of the well in the sensor unit actually used in the measuring apparatus (distance b in FIG. 1B) is 6.7 mm. In this case, the vertical position of the inner bottom surface of the well is deviated from the position determined on the basis of the position of the outer bottom surface of the sensor unit by 0.6 μm/° C., which corresponds to shift in reflection angle of the reflected light of 0.0004° (4 ORU).

SUMMARY OF THE INVENTION

In view of the foregoing observations and description, the primary object of the present invention is to provide a measuring apparatus in which deterioration of measuring accuracy due to displacement of the sensor unit is suppressed and the measuring accuracy is high.

In accordance with the present invention, there is provided a first measuring apparatus comprising a light source for emitting a light beam, a sensor unit comprising a dielectric block, a thin film layer, a sample holding portion and a reference surface for position measurement, the dielectric block being transparent to the light beam, the thin film layer being formed on the upper surface of the dielectric block, the sample holding portion being for holding a sample on the thin film layer and the reference surface for position measurement being coplanar with the upper surface of the dielectric block, a sensor holding means which removably holds the sensor unit in a predetermined position, a light beam projecting means which causes the light beam to enter the dielectric block to impinge upon the interface between the upper surface of the dielectric block and the thin film layer at an angle of incidence so that total internal reflection conditions are satisfied at the interface, a refractive index information obtaining means which obtains refractive index information on an analyte on the thin film layer on the basis of the light beam reflected at the interface, a displacement measuring means which measures displacement of the interface by measuring vertical displacement of the reference surface from a predetermined reference position, and a position adjustment means which mechanically adjusts the vertical position of the sensor unit according to the displacement of the reference surface measured by the displacement measuring means so that the reference surface is positioned in the predetermined reference position.

In the first measuring apparatus, the thin film layer may be of metal film. In this case, the first measuring apparatus is a surface plasmon resonance sensor which measures on the basis of the surface plasmon resonance. Further, in the first measuring apparatus, the thin film layer may comprise a clad layer formed on the upper surface of the dielectric block and an optical waveguide layer which is formed on the clad layer. In this case, the first measuring apparatus is a leaky mode sensor which measures on the basis of the effect of excitation of waveguide mode in the waveguide layer.

The expression "to obtain refractive index information on an analyte" should be broadly interpreted to include both "to obtain the refractive index of the sample disposed on the thin film layer" and "to fix on the thin film layer a sensing medium such as an antibody and to detect change in the refractive index of the sample containing therein the analyte such as antigen due to reaction of the sensing material with the analyte such as antigen-antibody reaction or to detect whether or not there is change of the refractive index due to reaction of the sensing material with the analyte such as antigen-antibody reaction.

The refractive index information maybe obtained by obtaining the refractive index or the change of the refractive index by causing a light beam to impinge upon the interface at various angles of incidence and detecting light beams reflected at the interface to detect the attenuation angle or change thereof or by obtaining the refractive index or the change of the refractive index by wavelengths by causing a plurality of light beams having different wavelengths to impinge upon the interface so that total internal reflection conditions are satisfied at the interface, measuring the intensities of the light beams reflected in total internal reflection at the interface by wavelengths and detecting the degree of attenuation in total internal reflection by wavelengths as disclosed in "Porous Gold in Surface Plasmon Resonance Measurement" by D. V. Noort, K. Johansen, and C. F. Mandenius (EUROSENSORS XIII, 1999, pp.585-588). Further, the refractive index information may be obtained by obtaining the change of the refractive index by causing a light beam to impinge upon the interface so that total internal reflection conditions are satisfied at the interface, splitting a part of the light beam before impinging upon the interface, causing the part of the light beam to interfere with the light beam reflected in total internal reflection at the interface, and detecting change of the interference fringe in the light beam after the interference as disclosed in "Surface Plasmon Resonance Interferometry for Micro-Array Biosensing" by P. I. Nikitin, A. N. Grigorenko, A. A. Beloglazov, M. V. Valeico, A. I. Savchuk, and O. A. Savchuk (EUROSENSORS XIII, 1999, pp.235-238).

That is, the "refractive index information on an analyte" may be any so long as it changes with change of the refractive index of the analyte, and may be, for instance, an attenuation angle or a wavelength of the light beam generating attenuation in total internal reflection which changes with change of the refractive index of the analyte, change of the attenuation angle or the wavelength of the light beam generating attenuation in total internal reflection or the change of the aforesaid interference fringe.

In accordance with the present invention, there is provided a second measuring apparatus comprising, a light source for emitting a light beam, a sensor unit comprising a dielectric block, a thin film layer, a sample holding portion and a reference surface for position measurement, the dielectric block being transparent to the light beam, the thin film layer being formed on the upper surface of the dielectric block, the sample holding portion being for holding a sample on the thin film layer and the reference surface for position measurement being coplanar with the upper surface of the dielectric block, a sensor holding means which removably holds the sensor unit in a predetermined position, a light beam projecting means which causes the light beam to enter the dielectric block to impinge upon the interface between the upper surface of the dielectric block and the thin film layer at various angles of incidence where total internal reflection conditions are satisfied at the interface, a displacement measuring means which measures displacement of the interface by measuring vertical displacement of the reference surface from a predetermined reference position, and an attenuation information obtaining means which obtains information on the attenuation angle by detecting the intensity of the light beam reflected at the interface, the information on the attenuation angle being corrected according to the displacement of the interface measured by the displacement measuring means to compensate for the displacement of the interface.

In the second measuring apparatus, the thin film layer may be of metal film. In this case, the second measuring apparatus is a surface plasmon resonance sensor which measures on the basis of the surface plasmon resonance. Further, in the second measuring apparatus, the thin film layer may comprise a clad layer formed on the upper surface of the dielectric block and an optical waveguide layer which is formed on the clad layer. In this case, the second measuring apparatus is a leaky mode sensor which measures on the basis of the effect of excitation of waveguide mode in the waveguide layer.

The expression "to obtain information on the attenuation angle" means to obtain information, for instance, on the refractive index of the analyte contained in the sample disposed on the thin film layer or on the change of the same by detecting the attenuation angle or the change of the same.

The expression "the information on the attenuation angle being corrected according to the displacement of the interface measured by the displacement measuring means" includes both the case where the intensity of the reflected light beam is first corrected on the basis of the displacement of the interface measured by the displacement measuring means and then the information on the attenuation angle is obtained on the basis of the corrected intensity of the reflected light beam and the case where the attenuation angle is obtained on the basis of the measured intensity of the reflected light beam and then the attenuation angle is corrected on the basis of the displacement of the interface measured by the displacement measuring means.

In the first and second measuring apparatuses, the expression "the reference surface for position measurement being coplanar with the upper surface of the dielectric block" means that the reference surface for measuring a position is coplanar with the upper surface of the dielectric block irrespective of thermal expansion of the sensor unit with change in temperature.

In the sensor unit, though the dielectric block, the thin film layer, the sample holding portion and the reference surface for measuring a position may be formed separately from each other and then bonded together, it is preferred from the viewpoint of handling that the sensor unit has a body into which at least the dielectric block and the sample holding portion are integrally formed. For example, the sensor unit comprises a body of dielectric material transparent to the light beam, a sample well is formed in the body in a predetermined depth to open in an upper surface of the body, a thin film layer is provided on the inner bottom surface of the sample well and a reference surface for position measurement is formed in the body in a position at a predetermined depth in parallel to the inner bottom surface of the sample well. In this case, a part of the body surrounding the sample well corresponds to the sample holding portion, a part of the body below the sample well corresponds to the dielectric block and the inner bottom surface of the sample well corresponds to the upper surface of the dielectric block. Further, the sensor unit may be provided with a plurality of one-dimensionally or two-dimensionally arranged sample wells.

The "predetermined reference position" may be either a position of the interface at a first time measurement or a position of the reference surface when the sensor unit is positioned in a sensor well setting position determined in advance by the measuring apparatus.

The displacement measuring means may comprise various distance sensors. However, it is preferred that the displacement measuring means comprises an electrostatic capacity type sensor probe fixed close to the reference surface. Further, an optical distance sensor which measures distance by causing a light beam to impinge upon the reference surface and receiving the light beam reflected at the reference surface may be used.

The position adjustment means may comprise a stage having a vertical axis and carrying thereon the sensor holding means. By driving the stage along the vertical axis to vertically move the sensor holding means, i.e., the sensor unit thereon, the vertical position of the interface of the sensor unit can be adjusted.

A configuration may be adopted wherein the sample holding means comprises a flow path member for forming a flow path on the thin film layer.

In accordance with the present invention, there is provided a sensor unit comprising a dielectric block transparent to the light beam, a thin film layer formed on the upper surface of the dielectric block, and a sample holding portion holding a sample on the thin film layer, characterized by having a reference surface for position measurement which is provided coplanar with the upper surface of the dielectric block in a position different from the interface between the upper surface of the dielectric block and the thin film layer.

The sensor unit may either be provided with only a single sample holding portion or a plurality of one-dimensionally or two-dimensionally arranged sample holding portions.

The dielectric block and the sample holding portion may be integrally formed with each other of the same dielectric material. For example, the sensor unit comprises a body of dielectric material transparent to the light beam, a sample well is formed in the body in a predetermined depth to open in an upper surface of the body, a thin film layer is provided on the inner bottom surface of the sample well and a reference surface for position measurement is formed in the body in a position at a predetermined depth in parallel to the inner bottom surface of the sample well.

When an electrostatic capacity type sensor probe or an optical distance sensor is employed for position measurement, a metal film such as of gold is deposited on the reference surface of the sensor unit.

A configuration may be adopted wherein the sample holding portion comprises a flow path member for forming a flow path on the thin film layer.

The sensor unit of the present invention may have a metallic film as the thin film layer. Thereby, the sensor unit may be constructed as a sensor unit to be employed in a surface plasmon resonance measuring apparatus that performs measurement by utilizing the aforementioned surface plasmon resonance effect.

Alternatively, the sensor unit of the present invention may have a cladding layer and an optical waveguide layer, which are formed on the upper surface of the dielectric block, as the thin film layer. Thereby, the sensor unit may be constructed as a sensor unit to be employed in a leaky mode measuring apparatus that performs measurement by utilizing an waveguide mode excitation effect of the optical waveguide layer.

In the first measuring apparatus of the present invention, since a sensor unit having a reference surface which is parallel to the surface that the thin film layer is formed on, and a displacement measuring means which measures the vertical displacement of the reference surface are provided, vertical displacement of the interface can be accurately measured without error due to thermal expansion of the sensor unit. Further, since a position adjustment means which adjusts the vertical position of the sensor unit to correct the displacement of the reference surface measured by the displacement measuring means is provided, when, for instance, measurement is performed a plurality of times on a sample at intervals to detect refractive index information such as the change of the refractive index during the interval, the measurement can be more accurately performed without error due to vertical displacement of the interface of the sensor unit.

In the second measuring apparatus of the present invention, since a sensor unit having a reference surface which is parallel to the surface that the thin film layer is formed on, and a displacement measuring means which measures the vertical displacement of the reference surface are provided, vertical displacement of the interface can be accurately measured without error due to thermal expansion of the sensor unit. Further, since the attenuation information obtaining means obtains corrected information on the attenuation angle corrected according to the displacement of the interface measured by the displacement measuring means, when, for instance, measurement is performed a plurality of times on a sample at intervals to detect refractive index information such as the change of the refractive index during the interval, the measurement can be more accurately performed without error due to vertical displacement of the interface of the sensor unit. Further, when the attenuation angle of a sample is measured to quantitatively analyze a sample, a result high in reliability can be obtained.

In the first and second measuring apparatuses of the present invention, a configuration may be adopted wherein the sample holding portion comprises a flow path member for forming a flow path on the thin film layer. In this case, measurement of samples that are likely to evaporate is facilitated.

In addition, the sample is only present within the narrow space of the flow path on the thin film layer during measurement. Therefore, the amount of the sample utilized during measurement can be decreased in comparison to a conventional sensor unit. At the same time, the need to consider concentration distributions within the well, which had been necessary with conventional sensor units, is obviated. Therefore, more accurate measurements are enabled.

In the sensor unit of the present invention, since the sensor unit has a reference surface which is parallel to the surface that the thin film layer is formed on, vertical displacement of the interface can be accurately measured without error due to thermal expansion of the sensor unit by detecting vertical displacement of the reference surface.

In the sensor unit of the present invention, a configuration may be adopted wherein the sample holding portion comprises a flow path member for forming a flow path on the thin film layer. In this case, measurement of samples that are likely to evaporate is facilitated.

In addition, the sample is only present within the narrow space of the flow path on the thin film layer during measurement. Therefore, the amount of the sample utilized during measurement can be decreased in comparison to a conventional sensor unit. At the same time, the need to consider concentration distributions within the well, which had been necessary with conventional sensor units, is obviated. Therefore, more accurate measurements are enabled.

Further, the flow path may be formed by providing the flow path member on the thin film layer after the thin film layer is formed on the dielectric block. Therefore, the flow path may be realized without deteriorating the processability of the thin film layer.

In accordance with the present invention, there is provided a third measuring apparatus comprising a light source for emitting a light beam, a sensor unit comprising a dielectric block transparent to the light beam, a thin film layer formed on the upper surface of the dielectric block, and a sample holding portion which holds a sample on the thin film layer, a sensor holding means which removably holds the sensor unit in a predetermined position, a light beam projecting means which causes the light beam to enter the dielectric block to impinge upon the interface between the upper surface of the dielectric block and the thin film layer at an angle of incidence so that total internal reflection conditions are satisfied at the interface, a refractive index information obtaining means which obtains refractive index information on a material on the thin film layer (analyte) by detecting the intensity of the light beam reflected at the interface, a temperature measuring means which measures the temperature of the sensor unit, a change calculating means which calculates change of the vertical distance between the interface and the reference surface of the sensor unit due to the difference of the temperature of the sensor unit measured by the temperature measuring means from a predetermined reference temperature, and a position adjustment means which mechanically adjusts the vertical position of the sensor unit according to the change of the vertical distance between the interface and the reference surface of the sensor unit calculated by the change calculating means so that the interface is positioned in a predetermined reference position.

In the third measuring apparatus, the thin film layer may be of metal film. In this case, the third measuring apparatus is a surface plasmon resonance sensor which measures on the basis of the surface plasmon resonance. Further, in the third measuring apparatus, the thin film layer may comprise a clad layer formed on the upper surface of the dielectric block and an optical waveguide layer which is formed on the clad layer. In this case, the third measuring apparatus is a leaky mode sensor which measures on the basis of the effect of excitation of waveguide mode in the waveguide layer.

The expression "to obtain refractive index information on an analyte" should be broadly interpreted to include both "to obtain the refractive index of the sample disposed on the thin film layer" and "to fix a sensing medium such as an antibody on the thin film layer and to detect change in the refractive index of the sample containing therein the analyte such as antigen due to reaction of the sensing material with the analyte such as antigen-antibody reaction or to detect whether or not there is change of the refractive index due to reaction of the sensing material with the analyte such as antigen-antibody reaction.

The refractive index information may be obtained by obtaining the refractive index or the change of the refractive index by causing a light beam to impinge upon the interface at various angles of incidence and detecting light beams reflected at the interface to detect the attenuation angle or change thereof or by obtaining the refractive index or the change of the refractive index by wavelengths by causing a plurality of light beams having different wavelengths to impinge upon the interface so that total internal reflection conditions are satisfied at the interface, measuring the intensities of the light beams reflected in total internal reflection at the interface by wavelengths and detecting the degree of attenuation in total internal reflection by wavelengths as disclosed in "Porous Gold in Surface Plasmon Resonance Measurement" by D. V. Noort, K. Johansen, and C. F. Mandenius (EUROSENSORS XIII, 1999, pp.585-588). Further, the refractive index information may be obtained by obtaining the change of the refractive index by causing a light beam to impinge upon the interface so that total internal reflection conditions are satisfied at the interface, splitting a part of the light beam before impinging upon the interface, causing the part of the light beam to interfere with the light beam reflected in total internal reflection at the interface, and detecting change of the interference fringe in the light beam after the interference as disclosed in "Surface Plasmon Resonance Interferometry for Micro-Array Biosensing" by P. I. Nikitin, A. N. Grigorenko, A. A. Beloglazov, M. V. Valeico, A. I. Savchuk, and O. A. Savchuk (EUROSENSORS XIII, 1999, pp.235-238).

That is, the "refractive index information on an analyte" may be any so long as it changes with change of the refractive index of the analyte, and may be, for instance, an attenuation angle or a wavelength of the light beam generating attenuation in total internal reflection which changes with change of the refractive index of the analyte, change of the attenuation angle or the wavelength of the light beam generating attenuation in total internal reflection or the change of the aforesaid interference fringe.

In accordance with the present invention, there is provided a fourth measuring apparatus comprising a light source for emitting a light beam, a sensor unit comprising a dielectric block transparent to the light beam, a thin film layer formed on the upper surface of the dielectric block, and a sample holding portion which holds a sample on the thin film layer, a sensor holding means which removably holds the sensor unit in a predetermined position, a light beam projecting means which causes the light beam to enter the dielectric block to impinge upon the interface between the upper surface of the dielectric block and the thin film layer at various angles of incidence where total internal reflection conditions are satisfied at the interface, an attenuation information obtaining means which obtains information on the attenuation angle by detecting the intensity of the light beam reflected at the interface, a temperature measuring means which measures the temperature of the sensor unit, and a change calculating means which calculates change of the vertical distance between the interface and the reference surface of the sensor unit due to the difference of the temperature of the sensor unit measured by the temperature measuring means from a predetermined reference temperature, wherein the attenuation information obtaining means obtains corrected information on the attenuation angle corrected according to the change of the vertical distance calculated by the change calculating means to compensate for the change of the vertical distance.

In the fourth measuring apparatus in accordance with the present invention, the thin film layer maybe of metal film. In this case, the fourth measuring apparatus is a surface plasmon resonance sensor which measures on the basis of the surface plasmon resonance. Further, in the fourth measuring apparatus, the thin film layer may comprise a clad layer formed on the upper surface of the dielectric block and an optical waveguide layer which is formed on the clad layer. In this case, the fourth measuring apparatus is a leaky mode sensor which measures on the basis of the effect of excitation of waveguide mode in the waveguide layer.

The expression "to obtain information on the attenuation angle" means to obtain information, for instance, on the refractive index of the analyte contained in the sample disposed on the thin film layer or on the change of the same by detecting the attenuation angle or the change of the same.

Note that in the third and fourth measuring apparatuses, a configuration may be adopted wherein the sample holding portion comprises a flow path member for forming a flow path on the thin film layer.

In the third measuring apparatus of the present invention, since a temperature measuring means which measures the temperature of the sensor unit, a change calculating means which calculates change of the vertical distance between the interface and the reference surface of the sensor unit due to the difference of the temperature of the sensor unit measured by the temperature measuring means from a predetermined reference temperature, and a position adjustment means which mechanically adjusts the vertical position of the sensor unit according to the change of the vertical distance between the interface and the reference surface of the sensor unit calculated by the change calculating means so that the interface is positioned in a predetermined reference position are provided, when, for instance, measurement is performed a plurality of times on a sample at intervals to detect change of the state of attenuation in total reflection during the interval, the measurement can be more accurately performed without error due to vertical displacement of the interface of the sensor unit.

In the fourth measuring apparatus of the present invention, since a temperature measuring means which measures the temperature of the sensor unit, and a change calculating means which calculates change of the vertical distance between the interface and the reference surface of the sensor unit due to the difference of the temperature of the sensor unit measured by the temperature measuring means from a predetermined reference temperature are provided and the attenuation information obtaining means obtains corrected information on the attenuation angle corrected according to the change of the vertical distance calculated by the change calculating means, when, for instance, measurement is performed a plurality of times on a sample at intervals to detect refractive index information such as the change of the refractive index during the interval, the measurement can be more accurately performed without error due to vertical displacement of the interface of the sensor unit.

In the third and fourth measuring apparatuses of the present invention, a configuration may be adopted wherein the sample holding portion comprises a flow path member for forming a flow path on the thin film layer. In this case, measurement of samples that are likely to evaporate is facilitated.

In addition, the sample is only present within the narrow space of the flow path on the thin film layer during measurement. Therefore, the amount of the sample utilized during measurement can be decreased in comparison to a conventional sensor unit. At the same time, the need to consider concentration distributions within the well, which had been necessary with conventional sensor units, is obviated. Therefore, more accurate measurements are enabled.

In accordance with the present invention, there is provided a fifth measuring apparatus comprising a light source for emitting a light beam, a sensor unit comprising a dielectric block, a thin film layer, and a sample holding portion which are formed integrally with each other, the dielectric block being transparent to the light beam, the thin film layer being formed on the upper surface of the dielectric block, and the sample holding portion holding a sample on the thin film layer, a sensor holding means which removably holds the sensor unit in a predetermined position, a light beam projecting means which causes the light beam to enter the dielectric block to impinge upon the interface between the upper surface of the dielectric block and the thin film layer at an angle of incidence so that total internal reflection conditions are satisfied at the interface, a refractive index information obtaining means which obtains refractive index information on an analyte on the thin film layer on the basis of the light beam reflected at the interface, a displacement measuring means which measures at least one of displacements of the interface from a predetermined reference position along one of axes Xw, Yw and Zw of an arbitrary orthogonal coordinate system and about the axes Xw, Yw and Zw, and a position adjustment means which mechanically adjusts the position of the sensor unit according to the displacement of the reference surface measured by the displacement measuring means so that the interface is positioned in the predetermined reference position.

In the fifth measuring apparatus, the thin film layer may be of metal film. In this case, the first measuring apparatus is a surface plasmon resonance sensor which measures on the basis of the surface plasmon resonance. Further, in the first measuring apparatus, the thin film layer may comprise a clad layer formed on the upper surface of the dielectric block and an optical waveguide layer which is formed on the clad layer. In this case, the first measuring apparatus is a leaky mode sensor which measures on the basis of the effect of excitation of waveguide mode in the waveguide layer.

The expression "to obtain refractive index information on an analyte" should be broadly interpreted to include both "to obtain the refractive index of the sample disposed on the thin film layer" and "to fix on the thin film layer a sensing medium such as an antibody and to detect change in the refractive index of the sample containing therein the analyte such as antigen due to reaction of the sensing material with the analyte such as antigen-antibody reaction or to detect whether or not there is change of the refractive index due to reaction of the sensing material with the analyte such as antigen-antibody reaction.

The refractive index information may be obtained by obtaining the refractive index or the change of the refractive index by causing a light beam to impinge upon the interface at various angles of incidence and detecting light beams reflected at the interface to detect the attenuation angle or change thereof or by obtaining the refractive index or the change of the refractive index by wavelengths by causing a plurality of light beams having different wavelengths to impinge upon the interface so that total internal reflection conditions are satisfied at the interface, measuring the intensities of the light beams reflected in total internal reflection at the interface by wavelengths and detecting the degree of attenuation in total internal reflection by wavelengths as disclosed in "Porous Gold in Surface Plasmon Resonance Measurement" by D. V. Noort, K. Johansen, and C. F. Mandenius (EUROSENSORS XIII, 1999, pp.585-588). Further, the refractive index information may be obtained by obtaining the change of the refractive index by causing a light beam to impinge upon the interface so that total internal reflection conditions are satisfied at the interface, splitting a part of the light beam before impinging upon the interface, causing the part of the light beam to interfere with the light beam reflected in total internal reflection at the interface, and detecting change of the interference fringe in the light beam after the interference as disclosed in "Surface Plasmon Resonance Interferometry for Micro-Array Biosensing" by P. I. Nikitin, A. N. Grigorenko, A. A. Beloglazov, M. V. Valeico, A. I. Savchuk, and O. A. Savchuk (EUROSENSORS XIII, 1999, pp.235-238).

That is, the "refractive index information on an analyte" may be any so long as it changes with change of the refractive index of the analyte, and may be, for instance, an attenuation angle or a wavelength of the light beam generating attenuation in total internal reflection which changes with change of the refractive index of the analyte, change of the attenuation angle or the wavelength of the light beam generating attenuation in total internal reflection or the change of the aforesaid interference fringe.

In accordance with the present invention, there is provided a sixth measuring apparatus comprising, a light source for emitting a light beam, a sensor unit comprising a dielectric block, a thin film layer, and a sample holding portion which are formed integrally with each other, the dielectric block being transparent to the light beam, the thin film layer being formed on the upper surface of the dielectric block, and the sample holding portion holding a sample on the thin film layer, a sensor holding means which removably holds the sensor unit in a predetermined position, a light beam projecting means which causes the light beam to enter the dielectric block to impinge upon the interface between the upper surface of the dielectric block and the thin film layer at various angles of incidence where total internal reflection conditions are satisfied at the interface, an attenuation information obtaining means which obtains information on the attenuation angle by detecting the intensity of the light beam reflected at the interface, and a displacement measuring means which measures at least one of displacements of the interface from a predetermined reference position along one of axes Xw, Yw and Zw of an arbitrary orthogonal coordinate system and about the axes Xw, Yw and Zw, wherein the attenuation information obtaining means obtains information on the corrected attenuation angle corrected according to the displacement of the interface measured by the displacement measuring means.

In the sixth measuring apparatus, the thin film layer may be of metal film. In this case, the sixth measuring apparatus is a surface plasmon resonance sensor which measures on the basis of the surface plasmon resonance. Further, in the sixth measuring apparatus, the thin film layer may comprise a clad layer formed on the upper surface of the dielectric block and an optical waveguide layer which is formed on the clad layer. In this case, the sixth measuring apparatus is a leaky mode sensor which measures on the basis of the effect of excitation of waveguide mode in the waveguide layer.

The expression "to obtain information on the attenuation angle" means to obtain information, for instance, on the refractive index of the analyte contained in the sample disposed on the thin film layer or on the change of the same by detecting the attenuation angle or the change of the same.

The expression "to obtain information on the corrected attenuation angle" includes both the case where the intensity of the reflected light beam is first corrected on the basis of the displacement of the interface measured by the displacement measuring means and then the information on the attenuation angle is obtained on the basis of the corrected intensity of the reflected light beam and the case where the attenuation angle is obtained on the basis of the measured intensity of the reflected light beam and then the attenuation angle is corrected on the basis of the displacement of the interface measured by the displacement measuring means.

Note that the fifth and sixth measuring apparatuses may adopt a configuration wherein the sample holding portion comprises a flow path member for forming a flow path on the thin film layer.

In the fifth and sixth measuring apparatuses, the "predetermined reference position" may be either a position of the interface at a first time measurement or a position of the reference surface when the sensor unit is positioned in a sensor well setting position determined in advance by the measuring apparatus.

The displacement measuring means may comprise various distance sensors. For example, the displacement measuring means may comprise an electrostatic capacity type sensor probe which measures displacement of the sensor unit in the direction of at least one of the Xw, Yw and Zw axes. Otherwise, the displacement measuring means may comprise a pair of electrostatic capacity type sensor probes which measure displacement of the sensor unit in the direction of at least one of the Xw, Yw and Zw axes in two positions and a rotational displacement calculating means which calculates displacement about at least one of the Xw, Yw and Zw axes on the basis of the measured values of the electrostatic capacity type sensor probes. Further, an optical lever type optical sensor which measures displacement about the Xw, Yw and Zw axes by causing a light beam to impinge upon a predetermined surface and receiving the light beam reflected at the predetermined surface may be used.

The position adjustment means may comprise a stage movable at least along the axis the displacement of the interface along which is measured by the displacement measuring means and carrying thereon the sensor holding means. By driving the stage to move the sensor holding means, i.e., the sensor unit thereon, in the respective axes, the position of the interface of the sensor unit can be adjusted.

The sensor unit may either be provided with only a single sample holding portion or a plurality of one-dimensionally or two-dimensionally arranged sample holding portions.

When an electrostatic capacity type sensor probe or an optical sensor is employed for position measurement, a metal film such as of gold is deposited on the measured surface of the sensor unit.

In the fifth measuring apparatus of the present invention, since a displacement measuring means which measures at least one of displacements of the interface from a predetermined reference position along one of axes Xw, Yw and Zw of an arbitrary orthogonal coordinate system and about the axes Xw, Yw and Zw and a position adjustment means which mechanically adjusts the position of the sensor unit according to the displacement of the reference surface measured by the displacement measuring means so that the interface is positioned in the predetermined reference position are provided, when, for instance, measurement is performed a plurality of times on a sample at intervals to detect refractive index information such as the change of the refractive index during the interval, the measurement can be more accurately performed without error due to displacement of the interface of the sensor unit.

In the sixth measuring apparatus of the present invention, since a displacement measuring means which measures at least one of displacements of the interface from a predetermined reference position along one of axes Xw, Yw and Zw of an arbitrary orthogonal coordinate system and about the axes Xw, Yw and Zw is provided and the attenuation information obtaining means obtains information on the corrected attenuation angle corrected according to the displacement of the interface measured by the displacement measuring means, when, for instance, measurement is performed a plurality of times on a sample at intervals to detect refractive index information such as the change of the refractive index during the interval, the measurement can be more accurately performed without error due to displacement of the interface of the sensor unit. Further, when the attenuation angle of a sample is measured to quantitatively analyze a sample, a result high in reliability can be obtained.

In the fifth and sixth measuring apparatuses of the present invention, a configuration may be adopted wherein the sample holding portion comprises a flow path member for forming a flow path on the thin film layer. In this case, measurement of samples that are likely to evaporate is facilitated.

In addition, the sample is only present within the narrow space of the flow path on the thin film layer during measurement. Therefore, the amount of the sample utilized during measurement can be decreased in comparison to a conventional sensor unit. At the same time, the need to consider concentration distributions within the well, which had been necessary with conventional sensor units, is obviated. Therefore, more accurate measurements are enabled.

BRIEF DESCRIPTION OF THE DRAWINGS

FIGS. 1A to 1C are a plan view, a front view and a side view of a sensor unit in accordance with a first embodiment of the present invention, FIG. 3 is a front view of the same, FIGS. 4A to 4C are a plan view, a front view and a side view schematically showing the positional relation between the sensor unit and the electrostatic probes and the optical angle displacement meter in the surface plasmon resonance sensor of the second embodiment, FIG. 6 is a side cross-sectional view of a surface plasmon resonance sensor in accordance with a third embodiment of the present invention, FIGS. 7A to 7C are a plan view, a front view and a side view schematically showing the positional relation between the sensor unit and the electrostatic probes and the optical angle displacement meter in the surface plasmon resonance sensor of the fourth embodiment, FIG. 8 is a side cross-sectional view of a leaky mode sensor in accordance with a fifth embodiment of the present invention, FIG. 9 is a side cross-sectional view of a measuring apparatus in accordance with the sixth embodiment of the present invention, FIG. 10 is a fragmentary front view of the measuring apparatus, FIG. 11 is a side cross-sectional view of a measuring apparatus in accordance with the seventh embodiment of the present invention, FIG. 13 is a front view showing an important part the sensor, FIGS. 14A to 14C are a plan view, a front view and a side view schematically showing the positional relation between the sensor unit and the electrostatic probes and the optical angle displacement meter in the surface plasmon resonance sensor.

DESCRIPTION OF THE PREFERRED EMBODIMENTS

Figure 2:
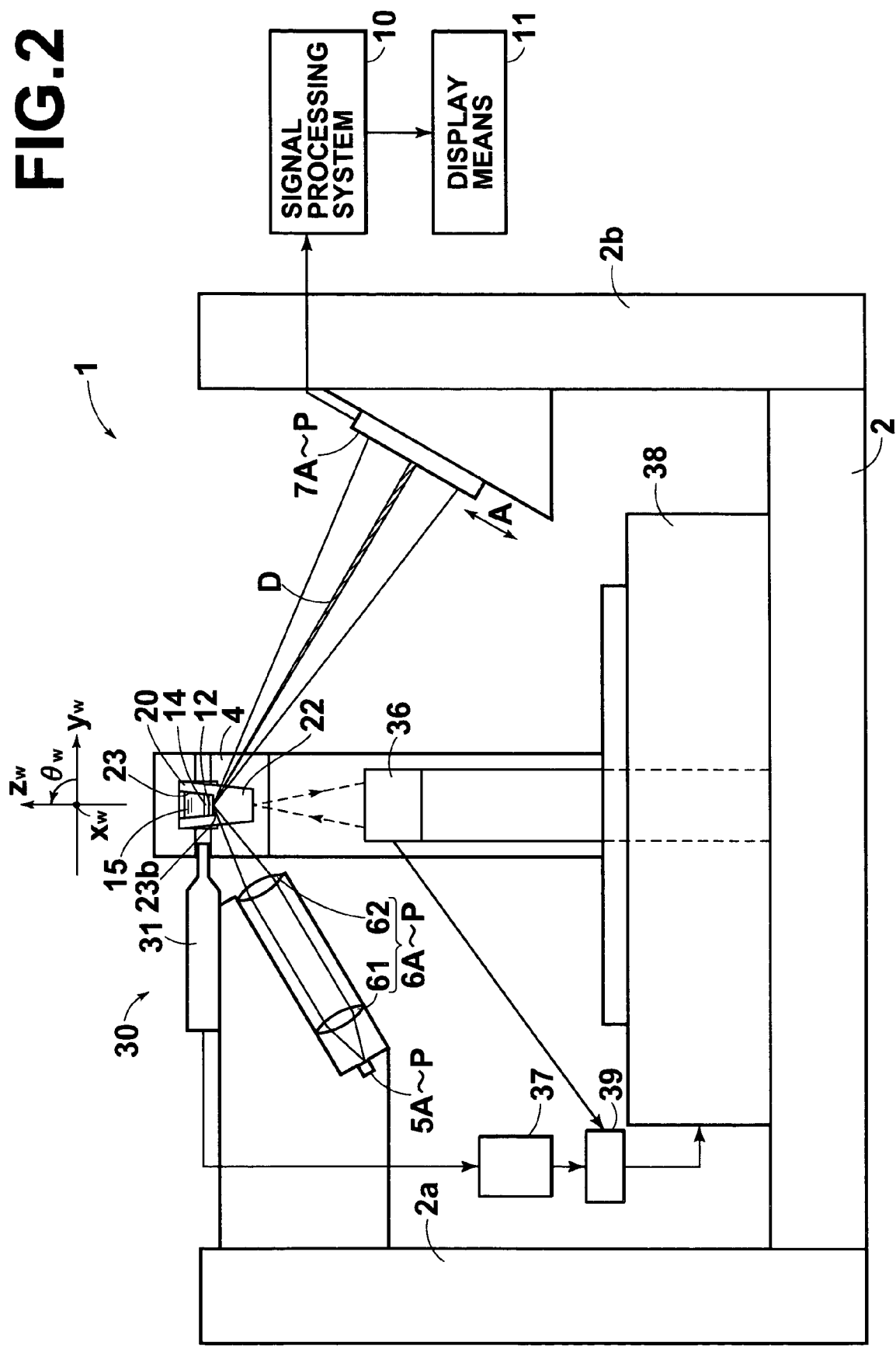
FIG. 2 is a side cross-sectional view of a surface plasmon resonance sensor in accordance with a second embodiment of the present invention employing the sensor unit 20 shown in FIGS. 1A to 1C of the first embodiment of the present invention.

In FIGS. 1A to 1C, a sensor unit 20 in accordance with a first embodiment of the present invention is provided with a body 21 formed of an elongated transparent dielectric material and a plurality of (e.g., 16) sample wells 23 are formed in the body 21 in a predetermined depth a to open in the upper surface 21a of the body 21. The sample wells 23 are arranged in a row and metal film 12 is coated on the inner bottom surface 23a of each of the sample wells 23 by deposition. That is, the body 21 comprises a dielectric block 22 transparent to a light beam (to be described later) and a sample holding portion 23' which forms the side surface of each sample well 23, which are formed integrally with each other, and the upper surface of the dielectric block 22 forms the inner bottom surface 23a of each of the sample wells 23. Accordingly, the metal film 12 coated on the inner bottom surface 23a of each of the sample wells 23 is metal film coated on the upper surface of the dielectric block 22, and the interface between the inner bottom surface 23a of each sample well 23 and the metal film 12 corresponds to the interface between the upper surface of the dielectric block 22 and the metal film 12.

The body 21 is formed, for instance, of transparent synthetic resin. Each sample well 23 is circular in cross-section and the diameter of each sample well 23 is reduced downward. In this particular embodiment, a sensing medium 14, which is combined with a particular material, is fixed on the metal film 12. Sample liquid containing therein an analyte is stored in each sample well 23.

First and second flanges 24 and 25 which are the same in thickness project outward respectively from the left and right ends of the body 21. The flanges 24 and 25 have upper surfaces 24a and 25a flush with the upper surface 21a of the body 21 and lower surfaces 24b and 25b parallel respectively to their upper surfaces 24a and 25a. Protrusions 26 and 27 having lower surfaces (reference surfaces) 26a and 27a which are flush with the inner bottom surface of the sample well 23 are respectively provided on the lower surfaces 24b and 25b of the first and second flanges 24 and 25. As will be described later, when only the vertical position is to be measured, only one of the protrusions 26 and 27 have to be provided.

FIG. 2 is a cross-sectional view of a surface plasmon resonance sensor in accordance with a second embodiment of the present invention employing the sensor unit 20 shown in FIGS. 1A to 1C of the first embodiment of the present invention, and FIG. 3 is a front view of the same.

The surface plasmon resonance sensor 1 of this embodiment comprises a sensor unit 20 described above, a platen 2, a sensor holding means 4 which is disposed on a six-axis fine-movement stage 38 to be described later and removably holds the sensor unit 20 in a predetermined position above the platen 2, light sources 5A, 5B, . . . 5P which are the same in number as the sample wells 23 and each of which emits a light beam L, light beam projecting means 6A, 6B, . . . 6P which cause the light beam L emitted from each of the light sources 5A, 5B, . . . 5P to enter the dielectric block to impinge upon the interface 23b between the upper surface of the dielectric block 22 and the thin film layer (metal film) 12 on the inner bottom surface 23a of the sample well 23 at various angles of incidence so that total internal reflection conditions are satisfied at the interface 23b, photodetectors 7A, 7B, . . . 7P each of which detects the light beam L reflected at the interface 23b, a signal processing system 10 which may be of a computer system and obtains attenuation information on the basis of the outputs of the photodetectors 7A, 7B, . . . 7P, a display means 11 connected to the signal processing system 10, a displacement measuring means 30 which measures displacement of the sensor unit 20 and a position adjustment means which comprises a six-axis fine-movement stage 38 disposed on the platen 2 and a drive means 39 which outputs a signal for driving the stage 38 and mechanically adjusts the position of the sensor unit 20. In this particular embodiment, the photodetectors 7A, 7B, . . . 7P and the signal processing system 10 form the attenuation information obtaining means.

In this embodiment, a plane parallel to the platen 2 is referred to as "XYw plane", the direction in which the light beam projecting means 6 (6A, 6B, . . . 6P), the sensor holding means 4 and the photodetector 7 (7A, 7B, . . . 7P) are arranged in the XYw plane is referred to as "Yw axis direction", a direction perpendicular to the Yw axis direction is referred to as "Xw axis direction" and a direction perpendicular to the XYw plane is referred to as "Zw axis direction". Further, the direction of rotation about the Xw axis or in the YZw plane is denoted by θw, the direction of rotation about the Yw axis or in the ZXw plane is denoted by φw, and the direction of rotation about the Zw axis or in the XYw plane is denoted by ψw.

The six-axis fine-movement stage 38 has six axes in the Xw direction, the Yw direction, the Zw direction and directions of rotation θw, φw and ψw and disposed so that the axes conforms to those determined on the basis of the platen 2.

The sensor holding means 4 supports the lower surfaces 24b and 25b of the first and second flanges 24 and 25 of the sensor unit 20 and supports the sensor unit 20 in a predetermined position above the platen 2 so that the sample wells 23 are arranged substantially along the Xw direction and the vertical displacement of the sensor unit 20 to the platen 2 is the displacement of the sensor unit 20 in the Zw direction. (FIGS. 2 and 3)

The light beam projecting means 6 (6A, 6B, . . . 6P) and the photodetector 7 (7A, 7B, . . . 7P) are fixed to the platen 2 by way of fixing portions 2a and 2b on opposite sides of the sensor holding means 4. Each of the light beam projecting means 6A, 6B, . . . 6P and each of the photodetectors 7A, 7B, . . . 7P are positioned to be aligned with one of the 16 sample wells 23.

Each of the light beam projecting means 6A, 6B, . . . 6P comprises a collimator lens 61 which converts the light beam L, emitted from the corresponding laser light source 5A, 5B, . . . 5P as a divergent light beam, into a parallel light, and a condenser lens 62 which condenses the light beam L.

The photodetector 7A comprises a line sensor formed of a plurality of photosensor elements which are arranged in a row extending in a direction perpendicular to the direction in which light beam L travels (the direction indicated by arrow A in FIG. 2). The line sensor may be a photodiode array or a CCD line sensor and the photodetector may comprise two-part photodiodes.

The displacement measuring means 30 comprises five electrostatic probes 31 to 35 and an optical angle displacement meter 36 which are fixed with respect to the platen 2, and a console 37 which controls the electrostatic probes 31 to 35 and measures displacements of the sensor unit 20 in the Xw direction, the Yw direction, the Zw direction and the directions of rotation θw, φw and ψw.

FIGS. 4A to 4C are a plan view, a front view and a side view schematically showing the positional relation between the sensor unit 20 set to the sensor holding means 4 and the electrostatic probes 31 to 35 and an optical angle displacement meter 36. As shown in FIGS. 4A to 4C, the sensor unit 20 is disposed so that the longitudinal direction of the sensor unit 20 extends along the Xw axis and the upper surface of the sensor unit 20 extends in perpendicular to the Zw axis.

An electrostatic probe 31 disposed to face a side surface 27b of the protrusion 27 of the sensor unit 20 (FIG. 4A) is for measuring the displacement of the sensor unit 20 in the direction of the Xw axis, and a pair of electrostatic probes 32 and 33 facing side surfaces 26c and 27c of the protrusions 26 and 27 of the sensor unit 20 (FIG. 4A) are for measuring the displacement of the sensor unit 20 in the direction of the Yw axis. On the basis of the outputs of the electrostatic probes 32 and 33, displacement of the sensor unit 20 from the reference position in the φw direction (the angle of rotation) can be known.

A pair of electrostatic probes 34 and 35 facing the lower surfaces 26a and 27a of the protrusions 26 and 27 of the sensor unit 20 (FIG. 4B) are for measuring the displacement of the sensor unit 20 in the direction of the Zw axis. On the basis of the outputs of the electrostatic probes 34 and 35, displacement of the sensor unit 20 from the reference position in the φw direction (the angle of rotation) can be known.

The electrostatic probes 31 to 35 which measure electrostatic capacity are generally 0.5 mm in diameter and ±25 µm in measuring full scale. However, the diameter and the measuring full scale of the electrostatic probes need not be limited to these values.

The console 37 generates electrostatic capacity between the sensor on the tip of the electrostatic probe and the surface and detects displacement of the surface as a change of the electrostatic capacity on the basis of the fact that the electrostatic capacity changes with the distance between the surface and the sensor, and outputs the displacement of the surface in terms of electric voltages. The lower surfaces 26a and 27a and the side surfaces 26c, 27c and 27b of the protrusions 26 and 27 of the sensor unit 20 the distances to which are to be measured are coated with metal film, e.g., of gold by deposition.

An optical angle displacement meter 36 positioned below the center of the sensor unit 20 in the Xw direction (FIG. 4C) is an optical lever type sensor, which detects displacement of the sensor unit 20 from the reference position in the θw direction (the angle of rotation) by causing a light beam to impinge upon the lower surface 21c of the sensor unit 20 at the center of the sensor unit 20 in the Xw direction and receiving the light beam reflected thereat. The part of the lower surface 21c of the sensor unit 20 at which the light beam impinges upon the sensor unit 20 is coated with metal film, e.g., of gold by deposition to form a mirror surface.

The drive means 39 outputs a signal for driving the stage 38 according to the displacement measured by the displacement measuring means 30 to return the sensor unit 20 to the reference position. The six-axis fine-movement stage 38 is driven upon receipt of the output of the drive means 39, and the position of the sensor holding means 4 on the stage 38 is finely adjusted to adjust the position of the interface of the sensor unit 20 held by the sensor holding means 4.

Though, in this embodiment, the position of the sensor unit 20 is measured and adjusted in all the directions, the measuring apparatus has only to measure and correct the displacement of the sensor unit 20 at least in the Zw axis.

Though, in this embodiment, displacement of the sensor unit in the Zw direction is measured in two positions in order to detect displacement in the ϕw direction in the XZw plane, displacement of the sensor unit in the Zw direction may be measured only in one position when it is not necessary to measure displacement in the ϕw direction. This is true of measurement of displacement in the Yw direction. In this case, only one of the protrusions 26 and 27 on the first and second flanges 24 and 25 has only to be formed.

In the conventional apparatus, displacement of the sensor unit in the Zw direction from the reference position has been measured with the lower surface 21c of the body 21 of the sensor unit 20 taken as the reference surface. Since the lower surface 21c is at a distance of b from the interface 23b, a difference is generated between displacement of the lower surface 21c in the Zw direction and displacement of the interface 23b in the Zw direction due to thermal expansion of the sensor unit 20, which can deteriorate accuracy of position adjustment. Whereas, in the measuring apparatus of this embodiment, since displacement in the Zw direction is measured on the basis of a reference surface (26a or 27a) which is coplanar with the interface 23b with respect to the position in the Zw direction, displacement of the interface 23b in the Zw direction can be more accurately measured and adjusted, whereby more accurate surface plasmon resonance measurement can be done.

Sample analysis by the surface plasmon resonance sensor of this embodiment will described, hereinbelow. Analysis of a sample by a sample well 23 in alignment with the light beam projecting means 6A and the photodetector 7A out of the sixteen sample wells 23 in the sensor unit 20 will be described by way of example, hereinbelow. However, analysis of a sample by other sample wells 23 is made in the same manner.

The light source 5A which maybe, for instance, a semiconductor laser, is driven and a light beam L is emitted from the light source 5A as a divergent light beam. The light beam L is collimated by a collimator lens 61 of the light beam projecting means 6A and is condensed by a condenser lens 62 to enter the dielectric block 22 as a convergent light beam and to impinge upon the interface 23b between the upper surface of the dielectric block 22 (the inner bottom surface 23a of each sample well 23) and the metal film 12 so that components impinging upon the interface at various angles of incidence of the light beam L to the interface 23b are included therein. The angle of incidence θ is in a range where total internal reflection conditions of the light beam L are satisfied and surface plasmon resonance is generated at the interfaces 23b. The inner bottom surface 23a of each of the sample wells 23 and the interface 23b may be considered to be substantially coplanar with each other.

The light beam L impinging upon the interface 23b is reflected in total internal reflection at the interface 23b and the reflected light beam L is detected by the photodetector 7A. Since the light beam L includes components impinging upon the interface 23b at various angles of incidence, the reflected light beam L includes components reflected at the interface 23b at various angles of reflection. In the photodetector 7A, different photosensor elements receive the components of the light beam L reflected at various angles of reflection and the photodetector 7A outputs a signal representing intensity distribution of the reflected light beam L received by the photosensor elements.

Figure 5:
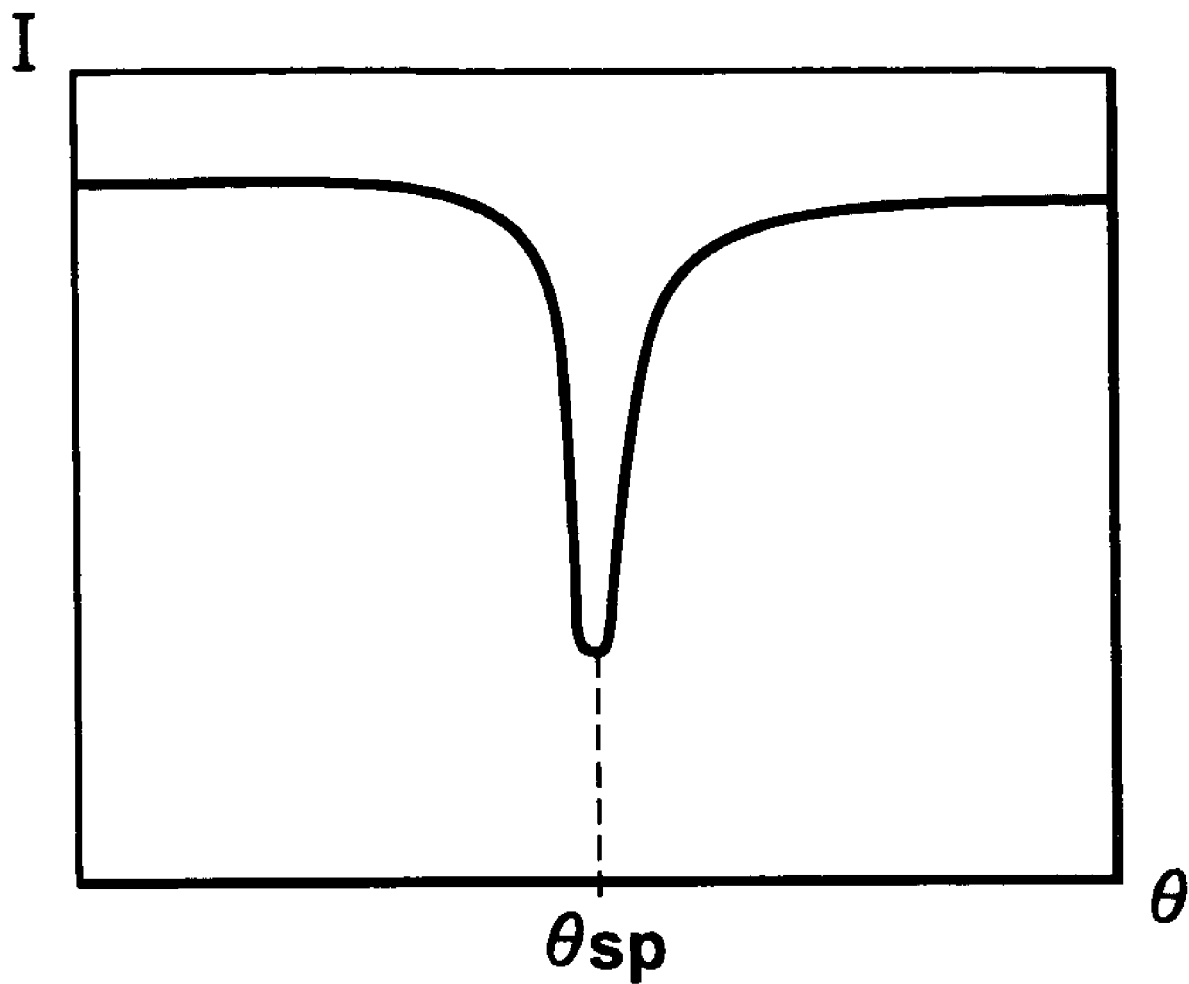
FIG. 5 is a view showing the relation between the angle of incidence θ of the light beam to the interface and the intensity I of the light beam received by the photodetector 7A.

The component of the light beam L impinging upon the interface 23b at a particular angle of incidence θsp excites surface plasmon in the interface between the metal film 12 and material in contact with the metal film 12 and the intensity of the component reflected in total internal reflection sharply drops. That is, the particular angle of incidence θsp is the attenuation angle or the angle at which the total internal reflection is cancelled and the intensity of the reflected light beam exhibits a minimum value at the angle of incidence θsp. The region where the intensity of the reflected light beam sharply drops is generally observed as a dark line D in the reflected light beam L. By detecting the amount of light detected by the photosensor elements on the basis of the signal output from the photodetector 7A, the attenuation angle θsp can be obtained on the basis of the position of the photosensor element detecting the dark line. FIG. 5 is a view showing the relation between the angle of incidence θ of the light beam L to the interface and the intensity I of the light beam received by the photodetector 7A. The attenuation angle θsp changes with change of the dielectric constant or the refractive index of the material in contact with the metal film 12 and moves right and left with change of the dielectric constant or the refractive index of the material in contact with the metal film 12. The angle of incidence θ and the particular angle of incidence θsp are referred to with respect to the angle of incidence of the light beam to the interface and have nothing to do with the θw direction (the angle of rotation) about the Zw axis described above.

The sensing medium 14 fixed to the surface of the metal film 12 in this embodiment combines a particular material and when a sample liquid containing therein the particular material is dropped on the sensing medium 14, the refractive index of the sensing medium 14 on the metal film 12 changes with change of the state of combination of the particular material with the sensing medium 14 and the curve shown in FIG. 5 moves right and left (that is, the attenuation angle θsp moves right and left). By measuring change of the attenuation angle θsp, whether the particular material is contained in the sample liquid 15 can be detected. In this case, both the sample liquid 15 and the sensing medium 14 are the object of analysis. As combinations of such a particular material and a sensing medium, for instance, combinations of an antigen and an antibody have been known.

On the basis of the principle described above, the signal processing system 10 detects the state of reaction of the particular material in the sample liquid 15 with the sensing medium 14, and causes the display means 11 to display the result of detection.

Such measurement is made in parallel to the other fifteen sample wells 23 and the sample liquid in the sixteen sample wells 23 are measured at one time. Projection of the light beam and detection of the attenuation angle θsp need not be done strictly at one time for the sixteen sample wells 23 but may be done at somewhat different times.

Whether there is contained in the sample liquid 15 particular material combined with the sensing medium 14 can be detected by measuring change of the attenuation angle θsp before and after the sample liquid is dispensed in the sixteen sample wells 23. In order to remove influence of the solvent of the sample liquid on the change of the refractive index, the measurement is done with buffer of the same components as the sample liquid stored in the sample well 23.

A certain time is required between measurement before dispensation of the sample liquid (before reaction) and measurement after dispensation of the sample liquid (after reaction) due to dispensation of the sample liquid and a predetermined reaction time. In order to better use the intervals between the measurement before reaction of the sample liquid and the measurement after reaction of the sample liquid, batch processing in which a sensor unit is once demounted from the measuring portion of a measuring apparatus after a measurement before reaction, another sensor unit is mounted on the measuring portion of the measuring apparatus, and then the measurement before reaction is made on said another sensor unit is generally carried out, thereby increasing the throughput capacity of the apparatus.

On the other hand, since the batch processing requires demounting and remounting the sensor unit, the position of the sensor unit or the interface in the measurement after reaction can be displaced from the position of the sensor unit or the interface in the measurement before reaction, which can deteriorate the measuring accuracy.

In the measuring apparatus of this embodiment, the displacement measuring means 30 and the position adjustment means prevent deterioration of the measuring accuracy due to the displacement of the interface as described above. Sample analysis of this measuring apparatus will be described hereinbelow.

Buffer solution is first dispensed by a dispenser in the sample wells 23 of a sensor unit 20 waiting in an incubator (not shown). Then the sensor unit 20 is conveyed to the sensor holding means 4 of the measuring apparatus 1 by a conveyor means and set there. The displacement measuring means 30 measures the position. In this particular embodiment, the position as measured at this time is the reference position.

Then the measurement before reaction is made on the sample wells 23 of the sensor unit 20.

After the measurement before reaction, the sensor unit 20 is returned to the incubator by the conveyor means and the sample liquid 15 is dispensed to the sample wells 23 thereof in the incubator.

Thereafter, the sensor unit 20 is again set to the sensor holding means 4 by the conveyor means. The time between the dispensation of the sample liquid 15 and the measurement after reaction may be determined according to the sample.

After the sensor unit 20 is again set to the sensor holding means 4, the displacement measuring means 30 again measures the position to obtain displacement from the reference position and outputs a signal based on the displacement to the drive means 39. The drive means 39 drives the six-axis fine-movement stage 38 on the basis of the signal to bring the sensor unit 20 to the reference position. At this time, the displacement measuring means 30 and the position adjustment means form a servo mechanism and the position measurement and the position adjustment are repeated until the sensor unit 20 is positioned in the reference position.

After the position of the sensor unit 20 is thus adjusted, the measurement after reaction is made on the sample liquid in the sample wells 23 of the sensor unit 20. The measurement after reaction is made with the particular material in the sample liquid 15 to be combined with the sensing medium 14 (if any) combined with the sensing medium 14, and by subtracting the measured value before reaction from the measured value after reaction, net change of the refractive index due to reaction of the analyte can be detected.

In this embodiment, since the sensor unit 20 is accurately positioned in the measurement after reaction in the same position as in the measurement before reaction, the result of detection is highly accurate.

As described above, the measurement before or after reaction on one or more sensor unit 20 is done between the measurement before reaction of a certain sensor unit 20 and the measurement after reaction of the certain sensor unit 20.

Though, in this embodiment, the reference position of the sensor unit 20 is determined before the measurement before reaction, the determination may be made at any time between the time the sensor unit 20 is mounted on the sensor holding means 4 and the time the sensor unit 20 is demounted from the sensor holding means 4, for instance, it may be done after the measurement before reaction or in parallel to the measurement before reaction.

Further, in place of determining the position of the sensor unit 20 in the measurement before reaction (first time measurement of the attenuation angle) as the reference position, the reference position may be determined in advance by the measuring apparatus.

Not only in the case where change of the refractive index between before and after reaction but also in the case where change with time of the reaction is to be detected, and measurement is to be done a plurality of times at predetermined intervals, the same setting position of the sensor unit 20 can be reproduced each time the sensor unit 20 is set to the sensor holding means 4. Further, also in quantitative analysis of the analyte based on the attenuation angle, the sensor unit 20 can be constantly positioned in a reference position and the attenuation angle for the sample can be accurately measured, whereby reliability of the measuring apparatus can be improved.

A surface plasmon resonance sensor in accordance with a third embodiment of the present invention will be described with reference to FIG. 6, hereinbelow. In FIG. 6, the elements analogous to those shown in FIG. 2 are given the same reference numerals and will not be described. Only the difference from the second embodiment will be mainly described hereinbelow.

The surface plasmon resonance sensor 51 differs from that of the second embodiment shown in FIG. 2 only in that the surface plasmon resonance sensor 51 of this embodiment is provided, in place of the position adjustment means, with a calculating means 10*a* which obtains change in the attenuation angle due to displacement of the interface and calculates a corrected measured value corrected to compensate for the change in the attenuation angle due to displacement of the interface.

The surface plasmon resonance sensor 51 of this embodiment corrects the measured value to compensate for the change in the attenuation angle due to displacement of the interface in the following manner. As in the second embodiment, the displacement measuring means 30 measures the position of a sensor unit 20 (the reference position) upon measurement before reaction on the sensor unit 20.

Then the displacement measuring means 30 obtains the displacements of the sensor unit 20 along the Xw axis, Yw axis and Zw axis and in the θw direction, the φw direction and the ϕw direction. The signal processing system 10 with the calculating means 10*a* obtains a corrected measured value corrected on the basis of the measuring error due to the displacement obtained by the displacement measuring means 30. That is, shift of angle of reflection of the light beam due to the displacements of the interface is obtained and the shift of angle of reflection of the light beam due to the displacements of the interface thus obtained is added to or subtracted from the attenuation angle as obtained from the output of the photodetector 7.

Since the measuring apparatus of this embodiment is provided with a sensor unit 20 and the displacement measuring means 30 similar to those in the first embodiment, and the displacement along the Zw axis of the reference surface 26*a* or 27*a* which is positioned in the same position as the interface in the Zw direction is measured, the displacement of the interface along the Zw axis can be accurately measured. Further, by virtue of the calculating means 10*a*, a corrected measured value accurately corrected on the basis of the measuring error due to the displacement can be obtained.

A surface plasmon resonance sensor in accordance with a fourth embodiment of the present invention will be described with reference to FIGS. 7A to 7C, hereinbelow. In this embodiment, the sensor unit differs from that in the first embodiment and accordingly in arrangement of the probes used to measure the displacement of the interface along the Zw axis. In FIGS. 7A to 7C, the elements analogous to those shown in FIG. 2 are given the same reference numerals and will not be described. Only the difference from the second embodiment will be mainly described hereinbelow. FIGS. 7A to 7C are a plan view, a front view and a side view schematically showing the positional relation between the sensor unit and the electrostatic probes and the optical angle displacement meter in the surface plasmon resonance sensor of the fourth embodiment.

In this embodiment, the sensor unit 120 is similar to the conventional one and differs from that shown in FIG. 1 in that no protrusion for position measurement is provided on the lower surface of the flange 24 nor 25. The electrostatic probe 31 for measurement of displacement along the Xw axis is fixed to the platen 2 to face a side surface 25*d* of the second flange 25 and the electrostatic probes 32 and 33 for measurement of displacements along the Yw axis and in the φw direction are fixed to the platen 2 to face a side surface 24*c* of the first flange 24 and a side surface 25*c* of the second flange 25. The side surfaces 24*c* and 25*c* of the first and second flanges 24 and 25 of the sensor unit 120 are provided with metal film by deposition.

Further, the electrostatic probes 34 and 35 for measurement of displacements along the Zw axis and in the ϕw direction are inserted into the outermost sample wells of the 16 sample wells 23 of the sensor unit 120 held by the sensor holding means 4 and measures displacement of the inner bottom surface 23*a* along the Zw axis. The outermost sample wells of the 16 sample wells 23 of the sensor unit 120 are not provided with the sensing medium 14 though provided with the metal film.

Also in this embodiment, since the displacement along the Zw axis is measured substantially in the position of the interface, the displacement along the Zw axis can be measured without being affected by errors due to thermal expansion of the sensor unit 120.

Though, in this embodiment, the outermost two sample wells of a plurality of sample wells 23 provided in the conventional sensor unit 120 are used to measure the displacement along the Zw axis, a sample well for position measurement having the same depth a as the sample wells 23 may be added on each or one end portion of the row of the sample wells 23 in order to avoid reduction of the number of the sample wells 23 available for measurement.

A leaky mode sensor in accordance with a fifth embodiment of the present invention will be described with reference to FIG. 8, which is a side cross-sectional view of a leaky mode sensor 101 in accordance with the fifth embodiment of the present invention, hereinbelow. In FIG. 8, the elements analogous to those shown in FIG. 2 are given the same reference numerals and will not be described. Only the difference from the second embodiment will be mainly described hereinbelow.

The measuring apparatus 101 is a leaky mode sensor described above and is provided with a sensor unit 20' provided with a plurality of sensor wells 23. However, a clad layer 40 is formed on the bottom surface of each sample well 23 in place of the metal film 12 and an optical waveguide layer 41 is formed on the clad layer 40. The arrangement of the other part is identical to the surface plasmon resonance sensor of the second embodiment.

In the leaky mode sensor of this embodiment, the body 21 of the sensor unit 20' is formed of synthetic resin or optical glass (e.g., BK7), and the clad layer 40 is in the form of film of dielectric material or metal (e.g., gold) which is lower in refractive index than the body 21. The optical waveguide layer 41 is in the form of film of dielectric material which is higher in refractive index than the clad layer 40 (e.g., PMMA). For example, the clad layer 40 is 36.5 nm in thickness when it is in the form of a metal film and the optical waveguide layer 41 is 700 nm in thickness when it is formed of PMMA.

In the leaky mode sensor with this arrangement, when the light beam L emitted from the light source 5 is caused to impinge upon the clad layer 40 through the dielectric block 22 at an angle not smaller than an angle of total internal reflection, the light beam L reflected in total reflection at the interface 23*b* between the dielectric block 22 and the clad layer 40 and the light having a particular wave number and impinging upon the optical waveguide layer 41 at a particular angle of incidence comes to propagate through the optical waveguide layer 41 in a waveguide mode after passing through the clad layer 40. When the waveguide mode is thus excited, almost all the incident light is taken in the optical waveguide layer 41 and accordingly, the intensity of light reflected in total internal reflection at the interface 23*b* sharply drops. That is, attenuation in total internal reflection occurs.

Since the wave number of light to be propagated through the optical waveguide layer 41 in a waveguide mode depends upon the refractive index of the sample 15 on the optical waveguide layer 41, the refractive index and/or the properties of the sample 15 related to the refractive index can be detected on the basis of the angle of incidence at which the attenuation in total internal reflection occurs. Further, by providing a sensing medium 14, which combines with a particular material on the optical waveguide layer 41, whether the sample liquid 15 includes the particular material can be detected as in the surface plasmon resonance sensor.

Also in the leaky mode sensor, by virtue of the displacement measuring means 30 and the position adjustment means, the displacement of the interface of the sensor unit 20' can be compensated for and accuracy of the measurement can be kept high.

A measuring apparatus in accordance with a sixth embodiment of the present invention will be described with reference to FIGS. 9 and 10, which are a side cross-sectional view and a fragmentary front view of a measuring apparatus 151 in accordance with the sixth embodiment of the present invention, hereinbelow.

The measuring apparatus 151 of this embodiment differs from the second embodiment in the structure of the displacement measuring means and the position adjustment means. In the measuring apparatus 151 of this embodiment, only the displacements along the Zw axis and in the θw direction are measured and position is adjusted with respect to the two axes. The two axes greatly concerns with the shift of angle of incidence of the light beam to the interface and the shift of angle of reflection of the light beam from the interface, and accordingly, the displacement along the axes must be more accurately controlled as compared with the other axes.

As the displacement measuring means 130, the measuring apparatus 151 of this embodiment comprises an optical distance sensor 131 which measures the displacement along the Xw axis. and an optical angle displacement meter 136 which measures the displacement in the θw direction.

The optical distance sensor 131 emits a light beam, traveling in the direction of the Zw axis, toward the lower surface 26*a* of the protrusion 26 for position measurement, and receives the light beam reflected at the lower surface 26*a*, thereby measuring the displacement of the reference surface 26*a* in the direction of the Zw axis. The optical angle displacement meter 136 emits a light beam toward the lower surface 27*a* of the protrusion 27 for position measurement on the other end, and receives the light beam reflected at the lower surface 26*a*, thereby measuring the displacement of the reference surface 27*a* in the θw direction.

The position adjustment means comprises a two-axis fine-movement stage 138 having two axes in the Zw axis direction and in the θw direction and a drive means 139 which drives the stage 138. The displacement measuring means 130 and the position adjustment means form a servo mechanism which adjusts the position of the sensor unit to a predetermined reference position. The predetermined reference position may be a position of the sensor unit when it is correctly set to the sensor holding means 4 or a position of the sensor unit upon the first time measurement out of positions upon measurement of a plurality of times.

The position of the sensor unit is first adjusted so that the reference surfaces 26*a* and 27*a*, which are displaced with displacement of the interface, are positioned in the reference positions and then the state of attenuation in total internal reflection is measured on each of the sample wells 23 (sample therein). By measuring after the position along the Zw axis and in the θw direction is thus adjusted, the measuring accuracy can be increased. The position adjustment of the sensor unit in the Zw axis direction is to move the whole sensor unit in parallel in the Zw axis direction.

Though, in the measuring apparatuses of the preceding embodiments described above, a light beam from a light source is caused to impinge upon the interface at various angles and the state of attenuation in total internal reflection is measured from the angle of incidence at which the light beam reflected at the interface appears as a dark line, whereby the state of combination of the analyte with the sensing medium is detected, the state of combination of the analyte with the sensing medium may be detected through the state of attenuation in total internal reflection by wavelength by causing light beams of different wavelengths to impinge upon the interface at a predetermined angle of incidence which satisfies the total internal reflection conditions, or by causing a light beam having a changing wavelength to impinge upon the interface, and by measuring the reflected light beam from the interface.

A measuring apparatus in accordance with a seventh embodiment of the present invention will be described with reference to FIG. 11, which is a side cross-sectional view of the measuring apparatus in accordance with the seventh embodiment of the present invention, hereinbelow. The measuring apparatus of this embodiment comprises, as that of the second embodiment, a sensor holding means 4 which holds a sensor unit 20, a displacement measuring means 30 and a position adjustment means. Since these elements are the same as those shown in FIG. 2, the method of measurement for obtaining the state of combination of the analyte with the sensing medium, which differs from the preceding embodiments, is only shown in FIG. 11 and will be described hereinbelow.

Light sources 320A to 320P, and CCDs 360A to 360P are disposed on opposite sides of the sensor unit 20. Collimator lenses 350A to 350P, interference optical systems, condenser lenses 355A to 355P, and apertures 356A to 356P are disposed between the light sources 320A to 320P, and the CCDs 360A to 360P.

The interference optical systems are formed by polarization filters 351A to 351P, half-silvered mirrors 352A to 352P, half-silvered mirrors 353A to 353P and mirrors 354A to 354P.

The CCDs 360A to 360P are connected to a signal processing section 361 and the signal processing section 361 is connected to a display means 362.

Measurement on samples by the measuring apparatus of this embodiment will be described, hereinbelow.

The light sources 320*a* to 320*e* are operated and light beams 330A to 330P are emitted therefrom as divergent light beams. The light beams 330A to 330P are collimated respectively by the collimator lenses 350A to 350P and impinge upon the polarization filters 351A to 351E. The light beams 330A to 330P polarized by the polarization filters 351A to 351P to impinge upon the interfaces in a p-polarized state are split into two light beams each by the half-silvered mirrors 352A to 352P. One of the two light beams is reflected by the corresponding one of the half-silvered mirrors 352A to 352P and forms a reference light beam 330R, whereas the other light beam 330S passes through the corresponding one of the half-silvered mirrors 352A to 352P and impinges upon corresponding one of the interfaces. Each of the light beams 330S reflected in total internal reflection at the interface and each of the reference light beams 330R reflected at mirrors 354A to 354P impinge upon corresponding one of the half-silvered mirrors 354A to 354P and synthesized into a light beam 330'. The synthesized light beam 330' is condensed by corresponding one of the condenser lenses 355A to 355P, and impinges upon the corresponding one of the CCDs 360A to 360P through the corresponding one of the apertures 356A to 356P. The light beam 330' detected by the corresponding one of the CCDs 360A to 360P generates interference fringes according to the state of interference of the light beam 330S and the reference light beam 330R.

By continuously measuring a plurality of times after the sample 15 is dispensed to detect the change of the interference fringes, bonding of the particular material with the sensing medium 14 can be detected. That is, since the refractive index of the sensing medium 14 changes with the state of bonding of the particular material with the sensing medium 14 and the state of the interference fringes generated by interference of the light beam 330S reflected in total internal reflection at the interface and the reference light beam 330R synthesized by corresponding one of the half-silvered mirrors 353A to 353P changes with the refractive index of the sensing medium 14, bonding of the particular material with the sensing medium 14 can be detected by detecting the change of the interference fringes.

The signal processing section 361 detects existence of the reaction on the basis of the above principle, and the display means 362 displays the result of the detection.

Also in this embodiment, by virtue of the displacement measuring means and the position adjustment means, the interface can be constantly held in a fixed position and an accurate measurement can be made, for instance, when existence of bonding of the particular material with the sensing medium is detected by demounting the sensor unit and mounting the same again.

Though, in the embodiments described above, the sensor unit is provided with a plurality of one-dimensionally arranged sample wells, a senor unit having only one sample well (the corresponding sample tip) or a plurality of two-dimensionally arranged sample wells may be employed.

Figure 12:
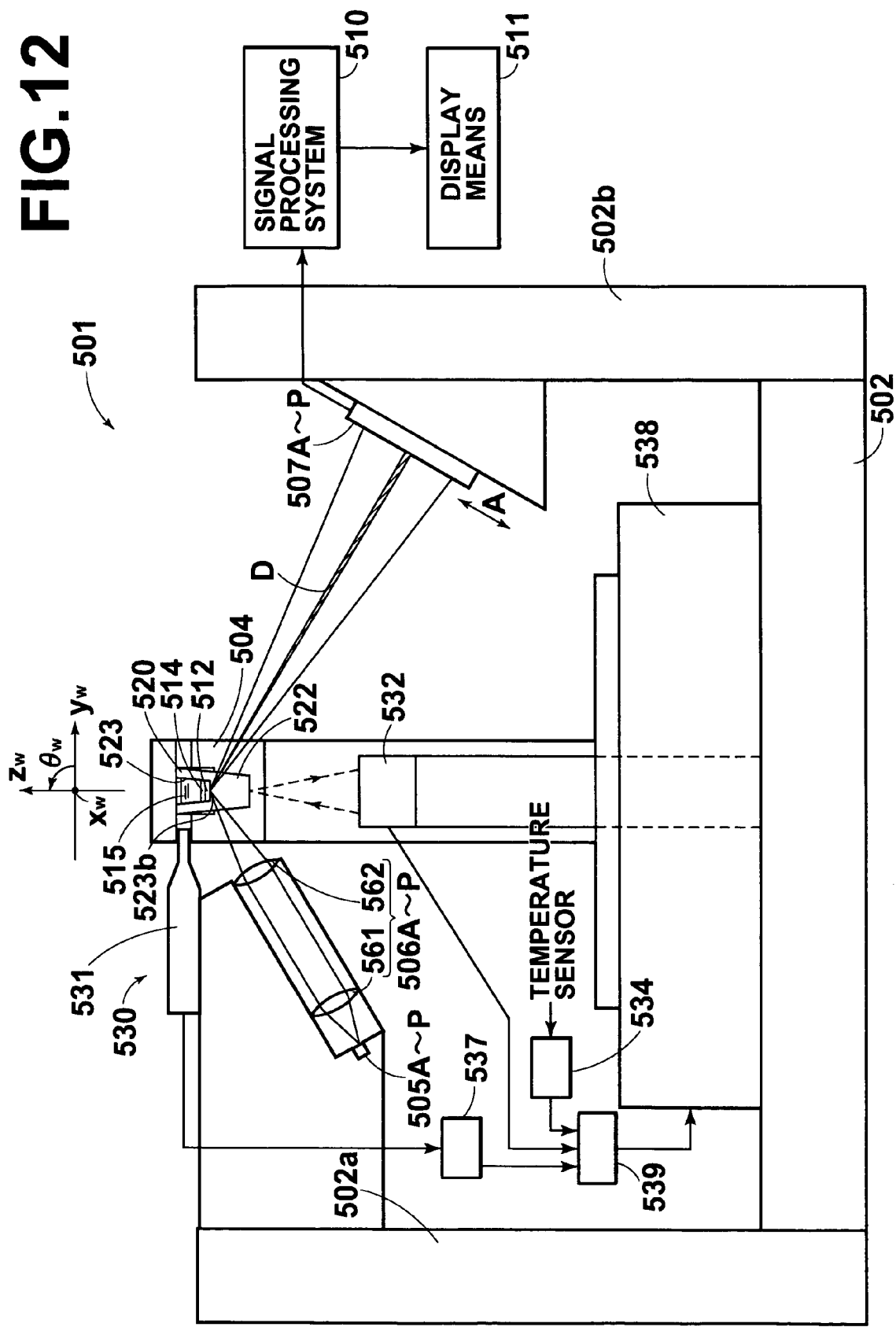
FIG. 12 is a cross-sectional view of a surface plasmon resonance sensor in accordance with an eighth embodiment of the present invention.
Figure 15:
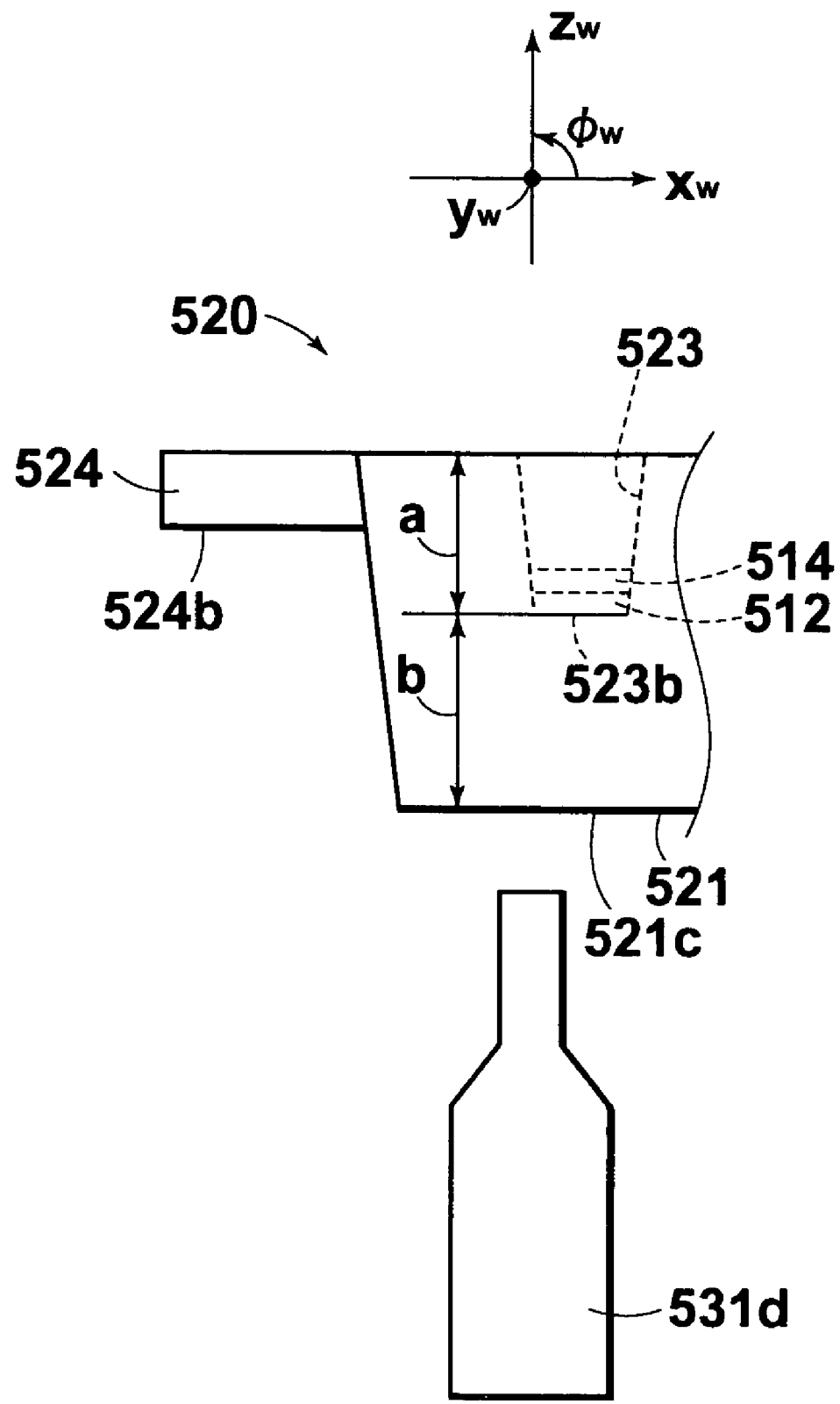
FIG. 15 is an enlarged view of the part of the sensor unit shown in FIG. 14B.

FIG. 12 is a cross-sectional view of a surface plasmon resonance sensor in accordance with an eighth embodiment of the present invention. FIG. 13 is a front view schematically showing the arrangement of the sensor unit and the displacement measuring means in the sensor. FIGS. 14A to 14C are a plan view, a front view and a side view schematically showing the positional relation between the sensor unit and the electrostatic probes and the optical angle displacement meter in the surface plasmon resonance sensor. FIG. 15 is an enlarged view of the part of the sensor unit shown in FIG. 14B.

The sensor unit 520 employed in the surface plasmon resonance sensor 501 of this embodiment will be described first. The sensor unit 520 is provided with a body 521 formed of an elongated transparent dielectric material and a plurality of (e.g., 16) sample wells 523 are formed in the body 521 in a predetermined depth a to open in the upper surface 521a of the body 521. The sample wells 523 are arranged in a row and metal film 512 is coated on the inner bottom surface 523a of each of the sample wells 523 by deposition. That is, the body 521 comprises a dielectric block 522 transparent to a light beam (to be described later) and a sample holding portion which forms the side surface of each sample well 523, which are formed integrally with each other, and the upper surface of the dielectric block 522 forms the inner bottom surface 523a of each of the sample wells 523. Accordingly, the metal film 512 coated on the inner bottom surface 523a of each of the sample wells 523 is metal film coated on the upper surface of the dielectric block 522, and the interface between the inner bottom surface 523a of each sample well 523 and the metal film 512 corresponds to the interface between the upper surface of the dielectric block 522 and the metal film 512. The outer bottom surface 521c of the body 521 of the sensor unit 520 forms the reference surface for position measurement.

The body 521 is formed, for instance, of transparent synthetic resin. Each sample well 523 is circular in cross-section and the diameter of each sample well 523 is reduced downward. In this particular embodiment, a sensing medium 514, which is combined with a particular material, is fixed on the metal film 512. For example, sample liquid containing therein an analyte is stored in each sample well 523.

First and second flanges 524 and 525 which are the same in thickness project outward respectively from the left and right ends of the body 521. The flanges 524 and 525 have upper surfaces 524a and 525a flush with the upper surface 521a of the body 521 and lower surfaces 524b and 525b parallel respectively to their upper surfaces 524a and 525a.

The surface plasmon resonance sensor 501 of this embodiment comprises a sensor unit 520 described above, a platen 502, a sensor holding means 504 which is disposed on a six-axis fine-movement stage 538 and removably holds the sensor unit 520 in a predetermined position above the platen 502, light sources 505A, 505B, . . . 505P which are the same in number as the sample wells 523 and each of which emits a light beam L, light beam projecting means 506A, 506B, . . . 506P which cause the light beam L emitted from each of the light sources 505A, 505B, . . . 505P to enter the dielectric block to impinge upon the interface 523b between the upper surface of the dielectric block 522 and the thin film layer (metal film) 512 on the inner bottom surface 523a of the sample well 523 at various angles of incidence so that total internal reflection conditions are satisfied at the interface 523b, photodetectors 507A, 507B, . . . 507P each of which detects intensity of the light beam L reflected at the interface 523b, a signal processing system 510 which maybe of a computer system and obtains attenuation information on the basis of the outputs of the photodetectors 507A, 507B, . . . 507P, a display means 511 connected to the signal processing system 10, a displacement measuring means 530 which measures displacement of the sensor unit 520, a temperature sensor 533 which measures the temperature of the sensor unit 520, a change calculating means 534 which calculates change of the vertical distance between the interface 523b and the reference surface 521c of the sensor unit 520 due to thermal expansion of the sensor unit 520, and a position adjustment means which comprises a six-axis fine-movement stage 538 disposed on the platen 2 and a drive means 539 which outputs a signal for driving the stage 538 and mechanically adjusts the position of the sensor unit 20.

In this particular embodiment, the photodetectors 507A, 507B, . . . 507P and the signal processing system 510 form the attenuation information obtaining means.

In this embodiment, a plane parallel to the platen 502 is referred to as "XYw plane", the direction in which the light beam projecting means 506 (506A, 506B, . . . 506P), the sensor holding means 504 and the photodetector 507 (507A, 507B, . . . 507P) are arranged in the XYw plane is referred to as "Yw axis direction", a direction perpendicular to the Yw axis direction is referred to as "Xw axis direction" and a direction perpendicular to the XYw plane is referred to as "Zw axis direction". Further, the direction of rotation about the Xw axis or in the YZw plane is denoted by θw, the direction of rotation about the Yw axis or in the ZXw plane is denoted by φw, and the direction of rotation about the Zw axis or in the XYw plane is denoted by ψw.

The six-axis fine-movement stage 538 has six axes in the Xw direction, the Yw direction, the Zw direction and directions of rotation θw, φw and ψw and disposed so that the axes conforms to those determined on the basis of the platen 502.

The sensor holding means 504 supports the lower surfaces 524b and 525b of the first and second flanges 524 and 525 of the sensor unit 520 and supports the sensor unit 520 in a predetermined position above the platen 502 so that the sample wells 523 are arranged substantially along the Xw direction and the vertical displacement of the sensor unit 520 to the platen 502 is the displacement of the sensor unit 520 in the Zw direction. (FIGS. 12 and 13) The temperature sensor 533 is installed at the part of the sensor holding means 504 holding the lower surface 525b of the flange 525 and measures the temperature of the sensor unit 520 while the sensor holding means 504 holds the sensor unit 520.

The light beam projecting means 506 (506A, 506B, . . . 506P) and the photodetector 507 (507A, 507B, . . . 507P) are fixed to the platen 502 by way of fixing portions 502a and 502b on opposite sides of the sensor holding means 504. Each of the light beam projecting means 506A, 506B, . . . 506P and each of the photodetectors 507A, 507B, . . . 507P are positioned to be aligned with one of the 16 sample wells 523.

Each of the light beam projecting means 506A, 506B, . . . 506P comprises a collimator lens 561 which converts the light beam L, emitted from the corresponding laser light source 505A, 505B, . . . 505P as a divergent light beam, into a parallel light, and a condenser lens 562 which condenses the light beam L.

The photodetector 507A comprises a line sensor formed of a plurality of photosensor elements which are arranged in a row extending in a direction perpendicular to the direction in which light beam L travels (the direction indicated by arrow A in FIG. 12). The line sensor may be a photodiode array or a CCD line sensor and the photodetector may comprise two-part photodiodes.

The displacement measuring means 530 comprises, as shown in FIGS. 14A to 14C, five electrostatic probes 531a to 531e and an optical angle displacement meter 532 which are fixed with respect to the platen 502, and a console 537 which controls the electrostatic probes 531a to 531e and measures displacements of the sensor unit 520 in the Xw direction, the Yw direction, the Zw direction and the directions of rotation $\theta w$, $\phi w$ and $\psi w$.

As shown in FIGS. 14A to 14C, the sensor unit 520 is disposed so that the longitudinal direction of the sensor unit 520 extends along the Xw axis and the upper surface of the sensor unit 520 extends in perpendicular to the Zw axis.

An electrostatic probe 531a disposed to face a side surface 525d of the second flange 525 of the sensor unit 520 (FIG. 14A) is for measuring the displacement of the sensor unit 520 in the direction of the Xw axis, and a pair of electrostatic probes 531b and 531c facing side surfaces 524c and 525c of the first and second flanges 524 and 525 of the sensor unit 520 in parallel to each other (FIG. 14A) are for measuring the displacement of the sensor unit 520 in the direction of the Yw axis. On the basis of the outputs of the electrostatic probes 531b and 531c, displacement of the sensor unit 520 from the reference position in the $\phi w$ direction (the angle of rotation) can be known.

A pair of electrostatic probes 531d and 531e facing the reference surface (outer bottom surface) 521c of the body 521 of the sensor unit 520 in parallel to each other (FIG. 14B) are for measuring the displacement of the sensor unit 520 in the direction of the Zw axis. On the basis of the outputs of the electrostatic probes 531d and 431e, displacement of the sensor unit 520 from the reference position in the $\phi w$ direction (the angle of rotation) can be known.

The electrostatic probes 531a to 531e which measure electrostatic capacity are generally 0.5 mm in diameter and ±25 µm in measuring full scale. However, the diameter and the measuring full scale of the electrostatic probes need not be limited to these values.

The console 537 generates electrostatic capacity between the sensor on the tip of each of the electrostatic probes 531a to 531e and the object surface and detects displacement of the object surface as a change of the electrostatic capacity on the basis of the fact that the electrostatic capacity changes with the distance between the object surface and the sensor, and outputs the displacement of the object surface in terms of electric voltages. The reference surface (the outer bottom surface) 521c of the body 521 and the side surfaces 524c, 525c and 525d the distances to which are to be measured are coated with metal film, e.g., of gold by deposition.

An optical angle displacement meter 532 positioned below the center of the sensor unit 520 in the Xw direction (FIG. 14C) is an optical lever type sensor, which detects displacement of the sensor unit 520 from the reference position in the $\theta w$ direction (the angle of rotation) by causing a light beam to impinge upon the reference surface 521c of the sensor unit 520 at the center of the sensor unit 520 in the Xw direction and receiving the light beam reflected thereat. The part of the reference surface 521c of the sensor unit 520 at which the light beam impinges upon the sensor unit 520 is coated with metal film, e.g., of gold by deposition to form a mirror surface.

The change calculating means 534 calculates change of the vertical distance between the interface 523b and the reference surface 521c of the sensor unit 520 (displacement of the interface 523b) due to thermal expansion of the sensor unit 520 by multiplying deformation per unit temperature of the section b (FIG. 15) between the reference surface 521c and the interface 523b, which has been determined in advance, by the value obtained by subtracting a predetermined reference temperature from the temperature of the sensor unit 520 measured by the temperature sensor 533.

The drive means 539 outputs a signal for driving the stage 538 according to the displacement of the sensor unit 520 measured by the displacement measuring means 530 and the displacement of the interface 523b due to thermal expansion of the sensor unit 520 calculated by the change calculating means 534 to return the interface 523b to the reference position (the position of the interface 523b when the sensor unit 520 is positioned in predetermined position at the reference temperature).

The six-axis fine-movement stage 538 is driven upon receipt of the output of the drive means 539, and the position of the sensor holding means 504 on the stage 538 is finely adjusted to adjust the position of the sensor unit 520 or the interface 523b thereon.

Though, in this embodiment, the position of the sensor unit 520 is measured and adjusted in all the directions, the measuring apparatus has only to measure and correct the displacement of the sensor unit 520 at least in the Zw axis.

Though, in this embodiment, displacement of the sensor unit in the Zw direction is measured in two positions in order to detect displacement in the $\phi w$ direction in the XZw plane, displacement of the sensor unit in the Zw direction may be measured only in one position when it is not necessary to measure displacement in the $\phi w$ direction. This is true of measurement of displacement in the Yw direction.

In the conventional apparatus, displacement of the sensor unit 520 in the Zw direction from the reference position has been measured on the basis of the reference surface 521c of the body 521 of the sensor unit 520. Since the reference surface 521c is at a distance of b from the interface 523b, a difference is generated between displacement of the lower surface 521c in the Zw direction and displacement of the interface 523b in the Zw direction due to thermal expansion of the sensor unit 520, which can deteriorate accuracy of position adjustment. Whereas, in the measuring apparatus of this embodiment, since the temperature of the sensor unit 520 is measured and the displacement of the interface 523b in the Zw direction from the reference surface 521c due to thermal expansion of the sensor unit 520 is calculated and corrected, displacement of the interface 23b in the Zw direction can be more accurately measured and adjusted, whereby more accurate surface plasmon resonance measurement can be done.

Sample analysis by the surface plasmon resonance sensor of this embodiment will described, hereinbelow. Analysis of a sample by a sample well 523 in alignment with the light beam projecting means 506A and the photodetector 507A out of the sixteen sample wells 523 in the sensor unit 520 will be described by way of example, hereinbelow. However, analysis of a sample by other sample wells 523 is made in the same manner.

The light source 505A which may be, for instance, a semiconductor laser, is driven and a light beam L is emitted from the light source 505A as a divergent light beam. The light beam L is collimated by a collimator lens 561 of the light beam projecting means 506A and is condensed by a condenser lens 562 to enter the dielectric block 522 as a convergent light beam and to impinge upon the interface 523b between the upper surface of the dielectric block 522 (the inner bottom surface 523a of each sample well 523) and the metal film 512 so that components impinging upon the interface at various angles of incidence of the light beam L to the interface 523b are included therein. The angle of incidence $\theta$ is in a range where total internal reflection conditions of the light beam L are satisfied and surface plasmon resonance is generated at the interfaces 523b. The inner bottom surface 523a of each of the sample wells 523 and the interface 23b maybe considered to be substantially coplanar with each other.

The light beam L impinging upon the interface 523b is reflected in total internal reflection at the interface 523b and the reflected light beam L is detected by the photodetector 507A. Since the light beam L includes components impinging upon the interface 523b at various angles of incidence, the reflected light beam L includes components reflected at the interface 523b at various angles of reflection. In the photodetector 507A, different photosensor elements receive the components of the light beam L reflected at various angles of reflection and the photodetector 507A outputs a signal representing intensity distribution of the reflected light beam L received by the photosensor elements.

The component of the light beam L impinging upon the interface 523b at a particular angle of incidence $\theta$sp excites surface plasmon in the interface between the metal film 512 and material in contact with the metal film 512 and the intensity of the component reflected in total internal reflection sharply drops. That is, the particular angle of incidence $\theta$sp is the attenuation angle or the angle at which the total internal reflection is cancelled and the intensity of the reflected light beam exhibits a minimum value at the angle of incidence $\theta$sp. The region where the intensity of the reflected light beam sharply drops is generally observed as a dark line D in the reflected light beam L. By detecting the amount of light detected by the photosensor elements on the basis of the signal output from the photodetector 507A, the attenuation angle $\theta$sp can be obtained on the basis of the position of the photosensor element detecting the dark line. FIG. 5 is a view showing the relation between the angle of incidence $\theta$ of the light beam L to the interface and the intensity I of the light beam received by the photodetector 507A.

The signal processing system 510 detects the state of reaction of the particular material in the sample liquid 515 with the sensing medium 514, and causes the display means 511 to display the result of detection.

Such measurement is made in parallel to the other fifteen sample wells 523 and the sample liquid in the sixteen sample wells 523 are measured at one time.

Whether there is contained in the sample liquid 515 particular material combined with the sensing medium 514 can be detected by measuring change of the attenuation angle $\theta$sp before and after the sample liquid is dispensed in the sixteen sample wells 523. In order to remove influence of the solvent of the sample liquid on the change of the refractive index, the measurement is done with buffer of the same components as the sample liquid stored in the sample well 523.

A certain time is required between measurement before dispensation of the sample liquid (before reaction) and measurement after dispensation of the sample liquid (after reaction) due to dispensation of the sample liquid and a predetermined reaction time. In order to better use the intervals between the measurement before reaction of the sample liquid and the measurement after reaction of the sample liquid, batch processing is generally carried out, thereby increasing the throughput capacity of the apparatus.

On the other hand, since the batch processing requires demounting and remounting the sensor unit, the position of the sensor unit or the interface in the measurement after reaction can be displaced from the position of the sensor unit or the interface in the measurement before reaction, which can deteriorate the measuring accuracy.

In the measuring apparatus of this embodiment, the displacement measuring means, the temperature sensor, the change calculating means and the position adjustment means prevent deterioration of the measuring accuracy due to the displacement of the interface as described above. Sample analysis of this measuring apparatus will be described hereinbelow.

Buffer solution is first dispensed by a dispenser in the sample wells 523 of a sensor unit 520 waiting in an incubator (not shown). Then the sensor unit 520 is conveyed to the sensor holding means 504 of the measuring apparatus 501 by a conveyor means and set there. The displacement measuring means 530 measures the position and the temperature sensor 533 measures the temperature. In this particular embodiment, the position and the temperature as measured at this time are the reference position and the reference temperature, respectively.

Then the measurement before reaction is made on the sample wells 523 of the sensor unit 520.

After the measurement before reaction, the sensor unit 520 is returned to the incubator by the conveyor means and the sample liquid 515 is dispensed to the sample wells 523 thereof in the incubator.

Thereafter, the sensor unit 520 is again set to the sensor holding means 504 by the conveyor means. The time between the dispensation of the sample liquid 515 and the measurement after reaction may be determined according to the sample.

After the sensor unit 520 is again set to the sensor holding means 504, the displacement measuring means 530 again measures the position to obtain displacement from the reference position and outputs a signal based on the displacement to the drive means 539. Further, the temperature sensor 533 measures the temperature of the sensor unit 520 and the change calculating means 534 calculates displacement of the interface 523b in the Zw axis direction from the reference surface 521c due to thermal expansion of the sensor unit 520 and outputs a signal based on the displacement to the drive means 539. The drive means 539 drives the six-axis fine-movement stage 538 on the basis of the signals from the displacement measuring means 530 and the change calculating means 534 to bring the sensor unit 520 to the reference position. At this time, the displacement measuring means 30 and the position adjustment means form a servo mechanism and the position measurement and the position adjustment are repeated until the sensor unit 520 is positioned in the reference position.

After the position of the sensor unit 520 is thus adjusted, the measurement after reaction is made on the sample liquid in the sample wells 523 of the sensor unit 520. The measurement after reaction is made with the particular material in the sample liquid 15 to be combined with the sensing medium 514 (if any) combined with the sensing medium 514, and by subtracting the measured value before reaction from the measured value after reaction, net change of the refractive index due to reaction of the analyte can be detected.

In this embodiment, since the sensor unit 520 is accurately positioned in the measurement after reaction in the same position as in the measurement before reaction, the result of detection is highly accurate.

As described above, the measurement before or after reaction on one or more sensor unit 520 is done between the measurement before reaction of a certain sensor unit 520 and the measurement after reaction of the certain sensor unit 520.

Though, in this embodiment, the reference position of the sensor unit 520 and the reference temperature are measured before the measurement before reaction, the measurement of the reference position and the reference temperature may be made at any time between the time the sensor unit 520 is mounted on the sensor holding means 504 and the time the sensor unit 520 is demounted from the sensor holding means 504, for instance, it may be done after the measurement before reaction or in parallel to the measurement before reaction.

Further, in place of determining the position of the sensor unit 520 in the measurement before reaction (first time measurement of the attenuation angle) as the reference position and the temperature as the reference temperature, the reference position and the reference temperature may be determined in advance by the measuring apparatus.

Not only in the case where change of the refractive index between before and after reaction but also in the case where change with time of the reaction is to be detected, and measurement is to be done a plurality of times at predetermined intervals, the same setting position of the sensor unit 520 can be reproduced each time the sensor unit 520 is set to the sensor holding means 504. Further, also in quantitative analysis of the analyte based on the attenuation angle, the sensor unit 520 can be constantly positioned in a reference position and the attenuation angle for the sample can be accurately measured, whereby reliability of the measuring apparatus can be improved.

Figure 16:
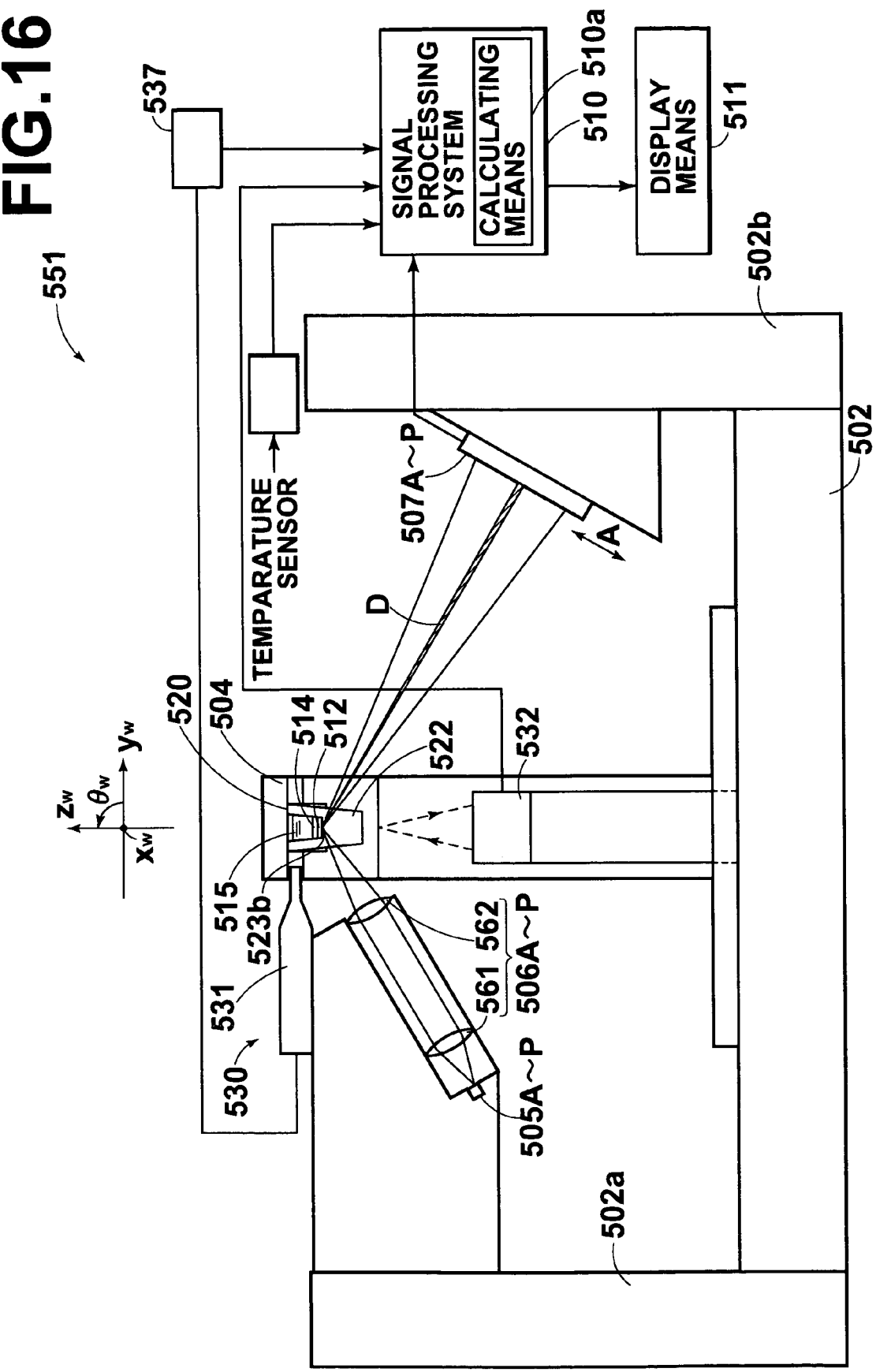
FIG. 16 is a side cross-sectional view of a surface plasmon resonance sensor in accordance with a ninth embodiment of the present invention.

A surface plasmon resonance sensor in accordance with a ninth embodiment of the present invention will be described with reference to FIG. 16, hereinbelow. In FIG. 16, the elements analogous to those shown in FIG. 12 are given the same reference numerals and will not be described. Only the difference from the eighth embodiment will be mainly described hereinbelow.

The surface plasmon resonance sensor 551 differs from that of the eighth embodiment shown in FIG. 12 only in that the surface plasmon resonance sensor 551 of this embodiment is provided, in place of the position adjustment means, with a calculating means 510a which obtains change in the attenuation angle due to displacement of the interface and calculates a corrected measured value corrected to compensate for the change in the attenuation angle due to displacement of the interface.

The surface plasmon resonance sensor 551 of this embodiment corrects the measured value to compensate for the change in the attenuation angle due to displacement of the sensor unit 520 in the following manner. As in the eighth embodiment, the displacement measuring means 30 measures the position of a sensor unit 520 and the temperature sensor 533 measures the temperature of the sensor unit 520 (the reference temperature) upon measurement before reaction on the sensor unit 520.

Then the displacement measuring means 530 obtains the displacements of the sensor unit 520 along the Xw axis, Yw axis and Zw axis and in the $\theta$w direction, the $\phi$w direction and the $\psi$w direction from the position in the measurement before reaction and the change calculating means 534 calculates the displacement of the interface 523b along the Zw axis from the reference surface 521c due to thermal expansion of the sensor unit 20. The signal processing system 510 with the calculating means 510a obtains a corrected measured value corrected on the basis of the measuring error due to the displacement obtained by the displacement measuring means 30 and the displacement obtained by the change calculating means 534. That is, shift of angle of reflection of the light beam due to the displacements of the interface is obtained and the shift of angle of reflection of the light beam due to the displacements of the interface thus obtained is added to or subtracted from the attenuation angle as obtained from the output of the photodetector 507.

Since the measuring apparatus of this embodiment is provided with a sensor unit 520, the displacement measuring means 530, the temperature sensor 533 and the change calculating means 534 similar to those in the eighth embodiment, and the displacement of the interface 523b along the Zw axis from the reference surface 521c due to thermal expansion of the sensor unit 520 is calculated and compensated for, the displacement of the interface 523b along the Zw axis can be accurately measured. Further, by virtue of the calculating means 510a, a corrected measured value accurately corrected on the basis of the measuring error due to the displacement can be obtained.

Figure 17:
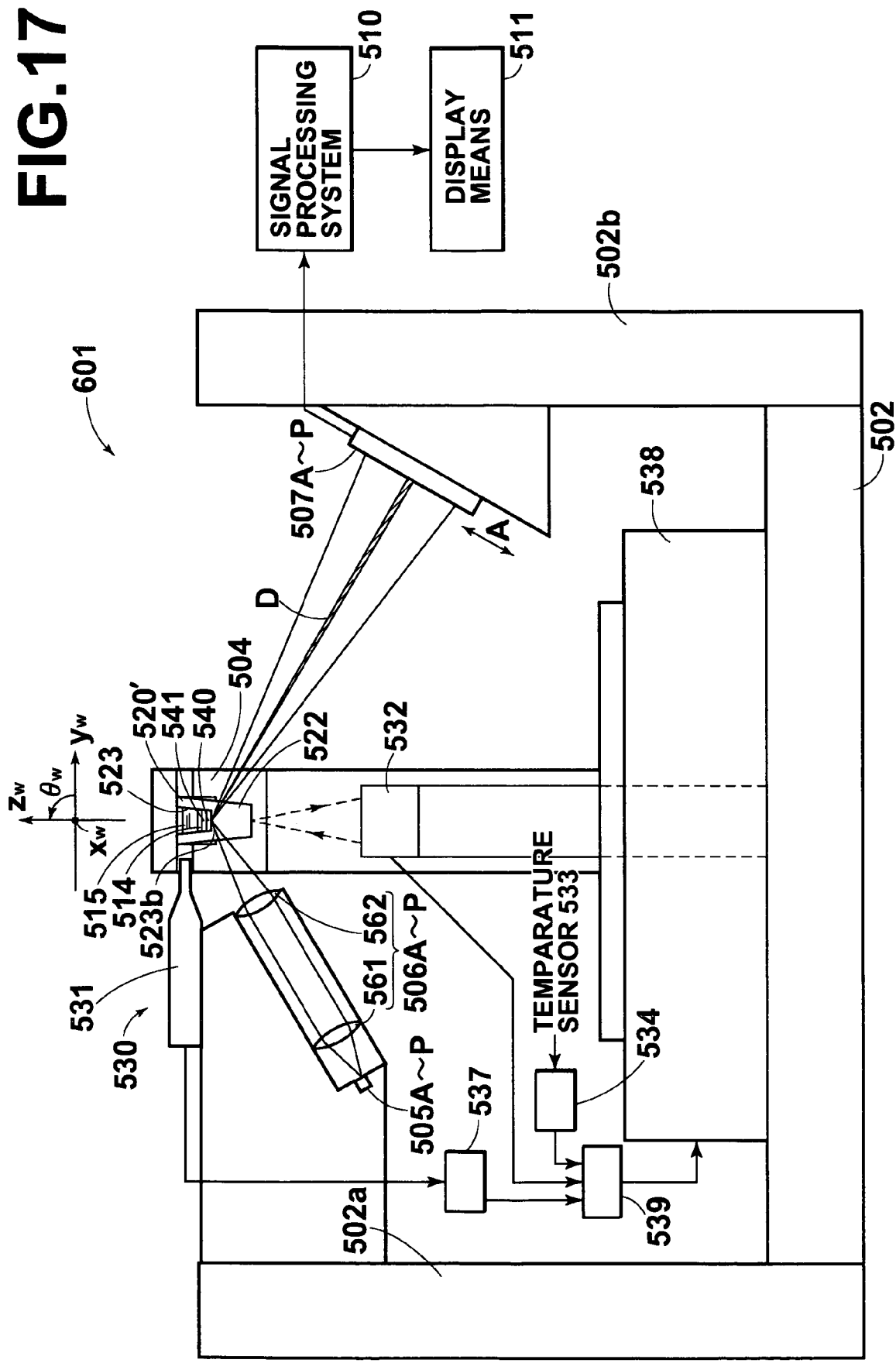
FIG. 17 is a side cross-sectional view of a leaky mode sensor in accordance with a tenth embodiment of the present invention.

A leaky mode sensor in accordance with a tenth embodiment of the present invention will be described with reference to FIG. 17, which is a side cross-sectional view of a leaky mode sensor 601 in accordance with the tenth embodiment of the present invention, hereinbelow. In FIG. 17, the elements analogous to those shown in FIG. 12 are given the same reference numerals and will not be described. Only the difference from the second embodiment will be mainly described hereinbelow.

The measuring apparatus 601 is a leaky mode sensor described above and is provided with a sensor unit 520' provided with a plurality of sensor wells 523. However, a clad layer 540 is formed on the bottom surface of each sample well 523 in place of the metal film and an optical waveguide layer 541 is formed on the clad layer 540. The arrangement of the other part is identical to the surface plasmon resonance sensor of the eighth embodiment.

In the leaky mode sensor of this embodiment, the body 521 of the sensor unit 520' is formed of synthetic resin or optical glass (e.g., BK7), and the clad layer 540 is in the form of film of dielectric material or metal (e.g., gold) which is lower in refractive index than the body 521. The optical waveguide layer 541 is in the form of film of dielectric material which is higher in refractive index than the clad layer 540 (e.g., PMMA). For example, the clad layer 540 is 36.5 nm in thickness when it is in the form of a metal film and the optical waveguide layer 541 is 700 nm in thickness when it is formed of PMMA.

In the leaky mode sensor with this arrangement, when the light beam L emitted from the light source 505 is caused to impinge upon the clad layer 540 through the dielectric block 522 at an angle not smaller than an angle of total internal reflection, the light beam L reflected in total reflection at the interface 523b between the dielectric block 522 and the clad layer 540 and the light having a particular wave number and impinging upon the optical waveguide layer 541 at a particular angle of incidence comes to propagate through the optical waveguide layer 541 in a waveguide mode after passing through the clad layer 540. When the waveguide mode is thus excited, almost all the incident light is taken in the optical waveguide layer 541 and accordingly, the intensity of light reflected in total internal reflection at the interface 523b sharply drops. That is, attenuation in total internal reflection occurs.

Since the wave number of light to be propagated through the optical waveguide layer 541 in a waveguide mode depends upon the refractive index of the sample 515 on the optical waveguide layer 541, the refractive index and/or the properties of the sample 515 related to the refractive index can be detected on the basis of the angle of incidence at which the attenuation in total internal reflection occurs. Further, by providing a sensing medium 514, which combines with a particular material on the optical waveguide layer 541, whether the sample liquid 515 includes the particular material can be detected as in the surface plasmon resonance sensor.

Also in the leaky mode sensor, by virtue of the displacement measuring means 530, the temperature sensor 533, the change calculating means 534 and the position adjustment means, the displacement of the interface of the sensor unit 520' can be compensated for and accuracy of the measurement can be kept high.

The sensor holding means which holds a sensor unit, the displacement measuring means, the temperature sensor, the change calculating means and a position adjustment means may be the same as those of the eighth embodiment with the method of measurement for obtaining the state of combination of the analyte with the sensing medium being the same as that described above in conjunction with FIG. 11.

Figure 18:
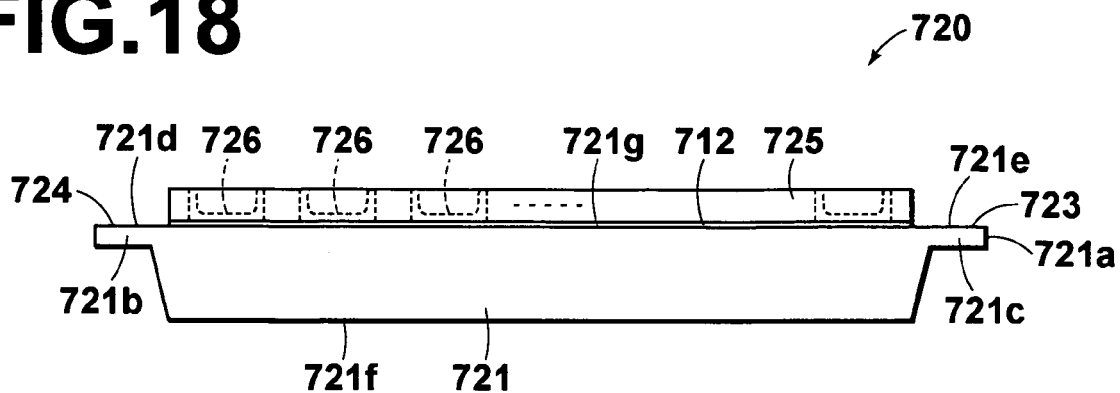
FIG. 18 is a front view of a sensor unit according to an eleventh embodiment of the present invention.
Figure 19:
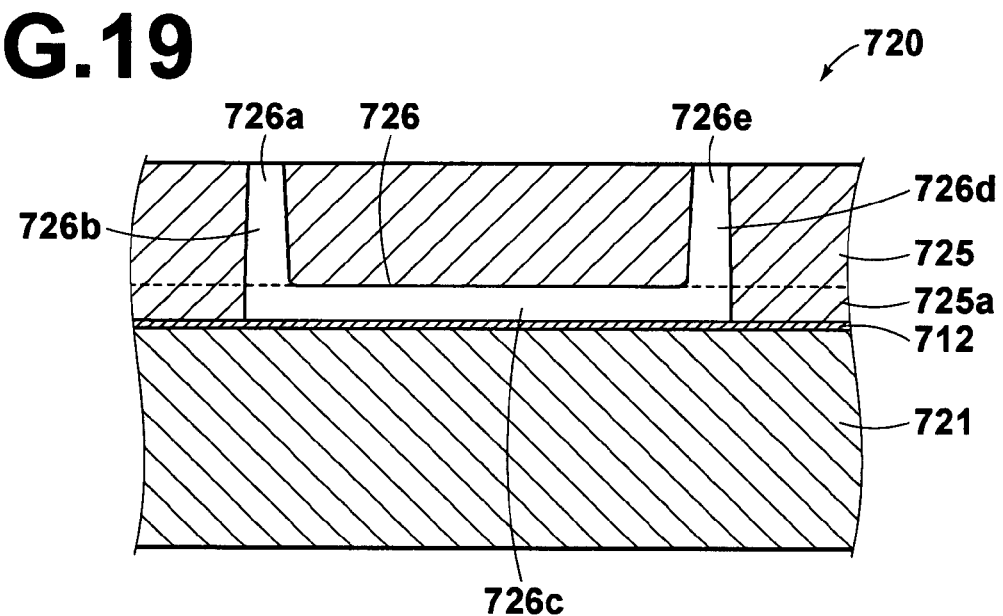
FIG. 19 is a partial sectional view of the sensor unit of the eleventh embodiment.

Yet another sensor unit will be described hereinbelow as the eleventh embodiment of the present invention. FIG. 18 is a front view of the sensor unit according to the eleventh embodiment. FIG. 19 is a partial sectional view of the sensor unit of the eleventh embodiment.

A sensor unit 720 is constituted by a dielectric block 721 (main body) and a flow path member 725. The dielectric block 721 is transparent with respect to light beams, and has a metallic film 712, as a thin film layer, formed on its flat upper surface 721g. The flow path member 725 is in close contact with the metallic film 712.

A first flange 723 extends from the left side of the main body 721, and a second flange 724 extends from the right side of the main body 721. The flanges 723 and 724 are of the same thickness, and have flat upper surfaces 721d and 721e, which are coplanar with the upper surface 721g of the main body 721, respectively. The upper surfaces 721d and 721e serve as reference surfaces to measure the position in the vertical direction, during measurement of a reference position.

The flow path member 725 comprises a plurality of linear flow paths 726 that extend in the longitudinal direction thereof. Each of the flow paths 726 comprises: an entrance 726a; a supply path 726 that leads from the entrance 726a to a measurement portion 726c; the measurement portion 726c; a discharge path 726d that leads from the measurement portion 726c to an exit 726e, and the exit 726e.

As illustrated in FIG. 19, an exit from the supply path 726b and an entrance to the discharge path 726d are open at the lower portion of the flow path member 725. Sealing members 725a that surround the exit from the supply path 726b and the entrance to the discharge path 726d are formed at a region that contacts the metallic film 712, which is positioned at the lower surface f the flow path member 725. The area between the sealing members 725a is the measurement portion 726c. For this reason, in the case that the flow path member 725 is in close contact with the metallic film 712 of the dielectric block 721, the measurement portion 726c functions as a portion of the flow path. That is, the flow path member functions as a sample holding portion. Note that the sealing members 725a may be integrally formed with the upper portion of the flow path member 725. Alternatively, the sealing members 725a may be formed by a different material from that of the upper portion, and added on later. For example, the sealing members 725a may be O-rings which are attached to the lower portion of the flow path member 725.

It is assumed that liquid samples including proteins are utilized in this sensor unit 720. However, accurate measurement becomes difficult if the proteins within the liquid sample become fixed within the flow paths 726. Therefore, it is preferable that the material of the flow path member 725 does not have nonsingular adsorption properties. Specific examples of such materials are silicon, polypropylene, and the like.

In the case that a sample is to be supplied to the sensor unit 720, a sample supplying pipette chip is inserted into the entrance 726a of the flow path 725, and a sample suctioning pipette chip is inserted into the exit 726e, to supply the sample to the measurement portion 726c of the flow path 726.

Figure 20:
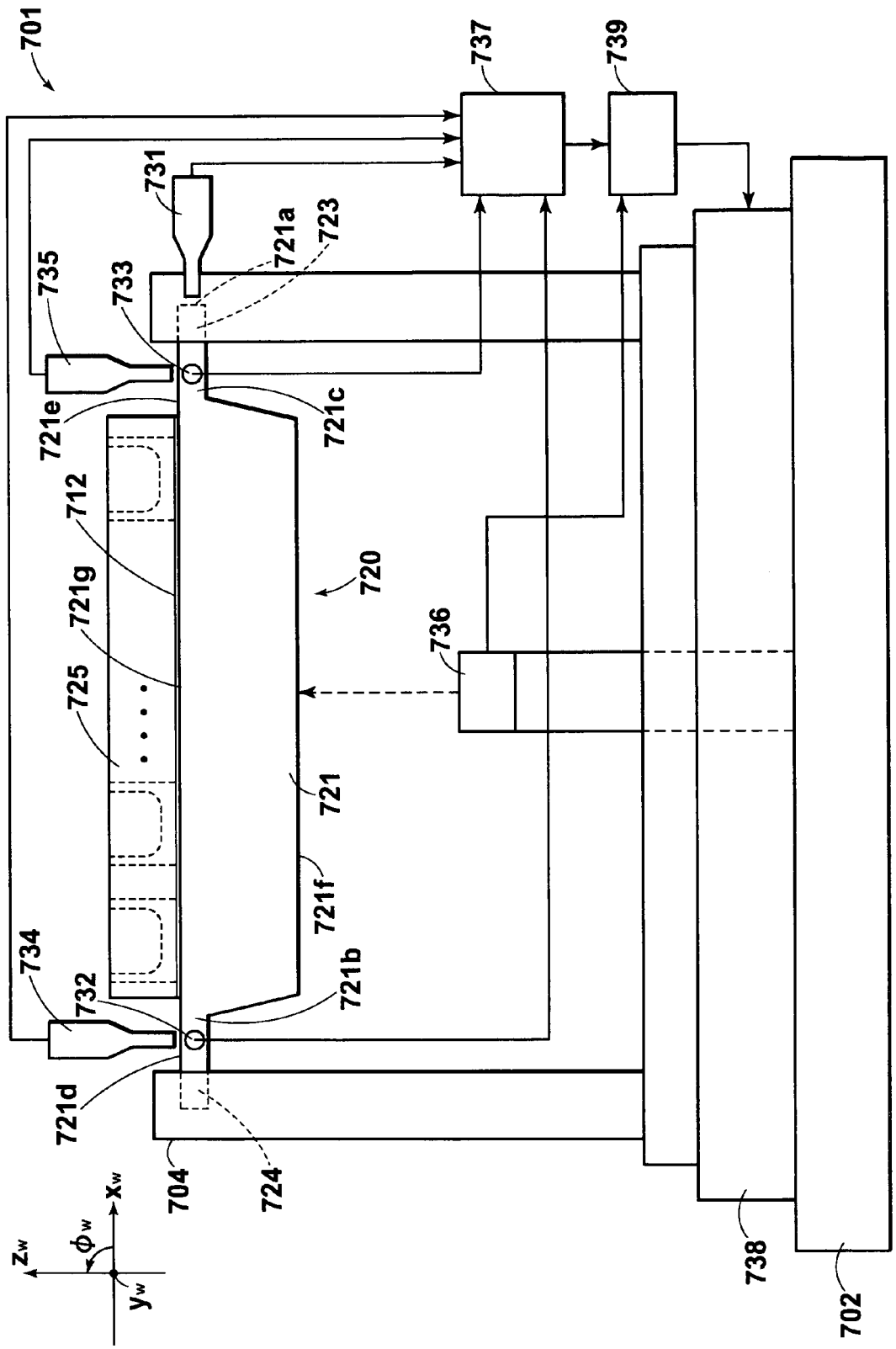
FIG. 20 is a front view showing the main parts of a surface plasmon resonance measuring apparatus according to a twelfth embodiment of the present invention.

FIG. 20 is a front view showing the schematic structure of a sensor unit and a displacement measuring means of a surface plasmon resonance measuring apparatus according to a twelfth embodiment of the present invention, which is equipped with the sensor unit 720. The measuring apparatus of the twelfth embodiment is of the same construction as the measuring apparatus of the second embodiment except for the arrangement of the displacement measuring means. Therefore, descriptions of other constituent parts of the measuring apparatus will be omitted insofar as they are not particularly necessary.

An electrostatic probe 731, which is provided to face a side surface 721a of the first flange 723 of the sensor unit 720, measures displacement of the sensor unit 720 in the direction of the Xw axis. Electrostatic probes 732 and 733, which are provided parallel to each other so as to face side surfaces 721b and 721c of the main body 721 of the sensor unit 720, measure displacement of the sensor unit 720 in the direction of the Yw axis. In addition, displacement in the $\phi w$ direction (angle of rotation) from a reference position of the sensor unit 720 can also be obtained from the outputs of the electrostatic probes 732 and 733.

Electrostatic probes 734 and 735, which are provided parallel to each other so as to face the upper surfaces 721d and 721e of the main body 721 of the sensor unit 720, measure displacement of the sensor unit 720 in the direction of the Zw axis. At the same time, displacement in the $\Phi w$ direction (angle of rotation) from a reference position of the sensor unit 720 can also be obtained from the outputs of the electrostatic probes 734 and 735.

An optical angle displacement meter 736, which is provided beneath the center, in the Xw direction, of the sensor unit 720, is an optical sensor of the optical lever type. The optical angle displacement meter 736 emits a light beam toward the center, in the Xw direction, of an outer bottom surface 721f of the sensor unit 720, and receives the light beam reflected therefrom. Thereby, the optical angle displacement meter 736 measures displacement of the sensor unit 720 in the θw direction (angle of rotation). Note that the portion of the outer bottom surface 721f, toward which the light beam is emitted, is formed as a mirror surface by vapor deposition of metal or the like.

The twelfth embodiment is equipped with the same displacement measuring means and position adjusting means as the measuring apparatus of the second embodiment. Thereby, the displacement of the interface of the sensor unit 720 can be compensated for, and accurate measurements are enabled.

Note that a plurality of linear flow paths 726 are provided in the flow path member 725 of the sensor unit 720. However, alternate configurations, wherein a single flow path 726 is provided, or a plurality of flow paths 726 are provided arranged in rows, are also possible.

In addition, the sensor unit 720 having the flow path member is not limited to being utilized by the measuring apparatus of the twelfth embodiment, in which a portion of the measuring apparatus of the second embodiment has been changed. The sensor unit 720 may be applied to all of the previously described measuring apparatuses. Note that in these cases, the positions of the electrostatic probes of the displacement measuring means may be changed as appropriate.

What is claimed is:

1. A measuring apparatus comprising:
   a light source for emitting a light beam,
   a sensor unit comprising a dielectric block, a thin film layer, a sample holding portion and a reference surface for position measurement, the dielectric block being transparent to the light beam, the thin film layer being formed on the upper surface of the dielectric block and being capable of generating surface plasmons, the sample holding portion being for holding a sample on the thin film layer and the reference surface for position measurement being coplanar with the upper surface of the dielectric block,
   a sensor holding means which removably holds the sensor unit in a predetermined position,
   a light beam projecting means which causes the light beam to enter the dielectric block to impinge upon the interface between the upper surface of the dielectric block and the thin film layer at an angle of incidence so that total internal reflection conditions are satisfied at the interface,
   a refractive index information obtaining means which obtains refractive index information on an analyte on the thin film layer on the basis of the light beam reflected at the interface,
   a displacement measuring means which measures displacement of the interface by measuring vertical displacement of the reference surface from a predetermined reference position, and
   a position adjustment means which mechanically adjusts the vertical position of the sensor unit according to the displacement of the reference surface measured by the displacement measuring means so that the reference surface is positioned in the predetermined reference position.

2. A measuring apparatus as defined in claim 1 in which the displacement measuring means comprises an electrostatic capacity type sensor probe fixed close to the reference surface to measure the distance to the reference surface.

3. A measuring apparatus as defined in claim 1, wherein: the sample holding portion comprises a flow path member for forming a flow path on the thin film layer.

4. A measuring apparatus as defined in claim 1, wherein the thin film layer comprises a metal film layer.

5. A measuring apparatus as defined in claim 1, wherein the thin film layer comprises a clad layer and an optical waveguide layer.

6. A measuring apparatus comprising:
   a light source for emitting a light beam,
   a sensor unit comprising a dielectric block, a thin film layer, a sample holding portion and a reference surface for position measurement, the dielectric block being transparent to the light beam, the thin film layer being formed on the upper surface of the dielectric block and being capable of generating surface plasmons, the sample holding portion being for holding a sample on the thin film layer and the reference surface for position measurement being coplanar with the upper surface of the dielectric block,
   a sensor holding means which removably holds the sensor unit in a predetermined position,
   a light beam projecting means which causes the light beam to enter the dielectric block to impinge upon the interface between the upper surface of the dielectric block and the thin film layer at various angles of incidence where total internal reflection conditions are satisfied at the interface,
   a displacement measuring means which measures displacement of the interface by measuring vertical displacement of the reference surface from a predetermined reference position,
   an attenuation information obtaining means which obtains information on the attenuation angle by detecting the intensity of the light beam reflected at the interface, the information on the attenuation angle being corrected according to the displacement of the interface measured by the displacement measuring means to compensate for the displacement of the interface; and
   a position adjustment means which mechanically adjusts the vertical position of the sensor unit according to the displacement of the reference surface measured by the displacement measuring means so that the reference surface is positioned in the predetermined reference position.

7. A measuring apparatus as defined in claim 6 in which the displacement measuring means comprises an electrostatic capacity type sensor probe fixed close to the reference surface to measure the distance to the reference surface.

8. A measuring apparatus as defined in claim 6, wherein: the sample holding portion comprises a flow path member for forming a flow path on the thin film layer.

9. A measuring apparatus as defined in claim 6, wherein the thin film layer comprises a metal film layer.

10. A measuring apparatus as defined in claim 6, wherein the thin film layer comprises a clad layer and an optical waveguide layer.

11. A sensor unit comprising a dielectric block transparent to a light beam, a thin film layer formed on the upper surface of the dielectric block and being capable of generating surface plasmons, and a sample holding portion holding a sample on the thin film layer,
    characterized by having a reference surface for position measurement which is provided coplanar with the upper surface of the dielectric block in a position different from the interface between the upper surface of the dielectric block and the thin film layer; and
    wherein a position of the sensor units mechanically adjusted according to a displacement of the reference surface so that the interface is positioned in a predetermined reference position prior to each measurement.

12. A sensor unit as defined in claim 11, wherein the sample holding portion comprises a flow path member for forming a flow path on the thin film layer.

13. A measuring apparatus as defined in claim 11, wherein the thin film layer comprises a metal film layer.

14. A measuring apparatus as defined in claim 11, wherein the thin film layer comprises a clad layer and an optical waveguide layer.

15. A measuring apparatus comprising:
a light source emitting a light beam,
a sensor unit comprising a dielectric block, a thin film layer, and a sample holding portion which are formed integrally with each other, the dielectric block being transparent to the light beam, the thin film layer being formed on the upper surface of the dielectric block and being capable of generating surface plasmons, and the sample holding portion holding a sample on the thin film layer,
a sensor holding means which removably holds the sensor unit in a predetermined position,
a light beam projecting means which causes the light beam to enter the dielectric block to impinge upon the interface between the upper surface of the dielectric block and the thin film layer at an angle of incidence so that total internal reflection conditions are satisfied at the interface,
a refractive index information obtaining means which obtains refractive index information on an analyte on the thin film layer on the basis of the light beam reflected at the interface,
a displacement measuring means which measures at least one of displacements of the interface from a predetermined reference position along one of axes Xw, Yw and Zw of an arbitrary orthogonal coordinate system and about the axes Xw, Yw and Zw, and
a position adjustment means which mechanically adjusts the position of the sensor unit according to the displacement of the reference surface measured by the displacement measuring means so that the interface is positioned in the predetermined reference position.

16. A measuring apparatus as defined in claim 15, wherein the displacement measuring means comprises an electrostatic capacity type sensor probe which measures displacement of the sensor unit in the direction of at least one of the Xw, Yw and Zw axes.

17. A measuring apparatus as defined in claim 15, wherein the displacement measuring means comprises a pair of electrostatic capacity type sensor probes which measure displacement of the sensor unit in the direction of at least one of the Xw, Yw and Zw axes in two positions and a rotational displacement calculating means which calculates displacement about at least one of the Xw, Yw and Zw axes on the basis of the values measured by the electrostatic capacity type sensor probes.

18. A measuring apparatus as defined in claim 15, wherein the displacement measuring means comprises an optical lever type optical sensor which measures displacement about the Xw, Yw and Zw axes by causing a light beam to impinge upon a predetermined surface and receiving the light beam reflected at the predetermined surface.

19. A measuring apparatus as defined in claim 15, wherein the sample holding portion comprises a flow path member for forming a flow path on the thin film layer.

20. A measuring apparatus as defined in claim 15, wherein the thin film layer comprises a metal film layer.

21. A measuring apparatus as defined in claim 15, wherein the thin film layer comprises a clad layer and an optical waveguide layer.

22. A measuring apparatus comprising,
a light source for emitting a light beam,
a sensor unit comprising a dielectric block, a thin film layer, and a sample holding portion which are formed integrally with each other, the dielectric block being transparent to the light beam, the thin film layer being formed on the upper surface of the dielectric block and being capable of generating surface plasmons, and the sample holding portion holding a sample on the thin film layer, a sensor holding means which removably holds the sensor unit in a predetermined position,
a light beam projecting means which causes the light beam to enter the dielectric block to impinge upon the interface between the upper surface of the dielectric block and the thin film layer at various angles of incidence where total internal reflection conditions are satisfied at the interface,
an attenuation information obtaining means which obtains information on the attenuation angle by detecting the intensity of the light beam reflected at the interface,
a displacement measuring means which measures at least one of displacements of the interface from a predetermined reference position along one of axes Xw, Yw and Zw of an arbitrary orthogonal coordinate system and about the axes Xw, Yw and Zw; and
a position adjustment means which mechanically adjusts the position of the sensor unit according to the displacement of the reference surface measured by the displacement measuring means so that the interface is positioned in the predetermined reference position, wherein:
the attenuation information obtaining means obtains information on the corrected attenuation angle corrected according to the displacement of the interface measured by the displacement measuring means.

23. A measuring apparatus as defined in claim 22, wherein the displacement measuring means comprises an electrostatic capacity type sensor probe which measures displacement of the sensor unit in the direction of at least one of the Xw, Yw and Zw axes.

24. A measuring apparatus as defined in claim 22, wherein the displacement measuring means comprises a pair of electrostatic capacity type sensor probes which measure displacement of the sensor unit in the direction of at least one of the Xw, Yw and Zw axes in two positions and a rotational displacement calculating means which calculates displacement about at least one of the Xw, Yw and Zw axes on the basis of the values measured by the electrostatic capacity type sensor probes.

25. A measuring apparatus as defined in claim 22, wherein the displacement measuring means comprises an optical lever type optical sensor which measures displacement about the Xw, Yw and Zw axes by causing a light beam to impinge upon a predetermined surface and receiving the light beam reflected at the predetermined surface.

26. A measuring apparatus as defined in claim 22, wherein the sample holding portion comprises a flow path member for forming a flow path on the thin film layer.

27. A measuring apparatus as defined in claim 22, wherein the thin film layer comprises a metal film layer.

28. A measuring apparatus as defined in claim 22, wherein the thin film layer comprises a clad layer and an optical waveguide layer.

29. A measuring apparatus as defined in claim 22, wherein the corrected attenuation angle is corrected by physical movement in along one of axes Xw, Yw and Zw.

30. A measuring apparatus comprising:

a light source for emitting a light beam, a sensor unit comprising a dielectric block transparent to the light beam, a thin film layer formed on the upper surface of the dielectric block and being capable of generating surface plasmons, a sample holding portion which holds a sample on the thin film layer and a reference surface for position measurement, a sensor holding means which removably holds the sensor unit in a predetermined position, a light beam projecting means which causes the light beam to enter the dielectric block to impinge upon the interface between the upper surface of the dielectric block and the thin film layer at an angle of incidence so that total internal reflection conditions are satisfied at the interface, a refractive index information obtaining means which obtains information on the refractive index of a material on the thin film layer by detecting the intensity of the light beam reflected at the interface, a temperature measuring means which measures the temperature of the sensor unit, a change calculating means which calculates change of the vertical distance between the interface and the reference surface of the sensor unit due to the difference of the temperature of the sensor unit measured by the temperature measuring means from a predetermined reference temperature, and a position adjustment means which mechanically adjusts the vertical position of the sensor unit according to the change of the vertical distance between the interface and the reference surface of the sensor unit calculated by the change calculating means so that the interface is positioned in a predetermined reference position.

31. A measuring apparatus as defined in claim 30, wherein the sample holding portion comprises a flow path member for forming a flow path on the thin film layer.

32. A measuring apparatus as defined in claim 30, wherein the thin film layer comprises a metal film layer.

33. A measuring apparatus as defined in claim 30, wherein the thin film layer comprises a clad layer and an optical waveguide layer.

34. A measuring apparatus comprising a light source for emitting a light beam, a sensor unit comprising a dielectric block transparent to the light beam, a thin film layer formed on the upper surface of the dielectric block and being capable of generating surface plasmons, a sample holding portion which holds a sample on the thin film layer and a reference surface for position measurement, a sensor holding means which removably holds the sensor unit in a predetermined position, a light beam projecting means which causes the light beam to enter the dielectric block to impinge upon the interface between the upper surface of the dielectric block and the thin film layer at various angles of incidence where total internal reflection conditions are satisfied at the interface, an attenuation information obtaining means which obtains information on the attenuation angle by detecting the intensity of the light beam reflected at the interface, a temperature measuring means which measures the temperature of the sensor unit, and a change calculating means which calculates change of the vertical distance between the interface and the reference surface of the sensor unit due to the difference of the temperature of the sensor unit measured by the temperature measuring means from a predetermined reference temperature; and a position adjustment means which mechanically adjusts the vertical position of the sensor unit according to the change of the vertical distance between the interface and the reference surface of the sensor unit calculated by the change calculating means so that the interface is positioned in a predetermined reference position, wherein:

the attenuation information obtaining means obtains corrected information on the attenuation angle corrected according to the change of the vertical distance calculated by the change calculating means to compensate for the change of the vertical distance.

35. A measuring apparatus as defined in claim 34, wherein the sample holding portion comprises a flow path member for forming a flow path on the thin film layer.

36. A measuring apparatus as defined in claim 34, wherein the thin film layer comprises a metal film layer.

37. A measuring apparatus as defined in claim 34, wherein the thin film layer comprises a clad layer and an optical waveguide layer.

* * * * *